(12) United States Patent
Franchini et al.

(10) Patent No.: US 7,094,408 B2
(45) Date of Patent: Aug. 22, 2006

(54) IMMUNOGENICITY USING A COMBINATION OF DNA AND VACCINIA VIRUS VECTOR VACCINES

(75) Inventors: Genoveffa Franchini, Washington, DC (US); Zdenek Hel, Rockville, MD (US); George Pavlakis, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 105 days.

(21) Appl. No.: 10/258,570

(22) PCT Filed: Apr. 30, 2001

(86) PCT No.: PCT/US01/13968

§ 371 (c)(1),
(2), (4) Date: Oct. 25, 2002

(87) PCT Pub. No.: WO01/82964

PCT Pub. Date: Nov. 8, 2001

(65) Prior Publication Data

US 2004/0033237 A1     Feb. 19, 2004

Related U.S. Application Data

(60) Provisional application No. 60/200,444, filed on Apr. 28, 2000.

(51) Int. Cl.
*A61K 39/00*     (2006.01)
(52) U.S. Cl. .................. 424/192.1; 424/188.1; 424/208.1; 424/192.1; 435/235.1; 435/320.1; 536/23.72; 514/44; 530/826
(58) Field of Classification Search ........... 530/826; 435/235.1, 320.1; 536/23.72; 424/188.1, 424/192.1, 208.1; 514/44
See application file for complete search history.

(56) References Cited

U.S. PATENT DOCUMENTS

| | | |
|---|---|---|
| 4,235,871 A | 11/1980 | Papahadjopoulos et al. |
| 4,501,728 A | 2/1985 | Geho et al. |
| 4,603,112 A | 7/1986 | Paoletti et al. |
| 4,722,848 A | 2/1988 | Paoletti et al. |
| 4,769,330 A | 9/1988 | Paoletti et al. |
| 4,837,028 A | 6/1989 | Allen |
| 5,019,369 A | 5/1991 | Presant et al. |
| 5,110,587 A | 5/1992 | Paoletti et al. |
| 5,174,993 A | 12/1992 | Pailetti |
| 5,187,074 A | 2/1993 | Treiber et al. |
| 5,192,668 A | 3/1993 | Treiber et al. |
| 5,204,253 A | 4/1993 | Sanford et al. |
| 5,279,833 A | 1/1994 | Rose |
| 5,308,854 A | 5/1994 | Hoffman, Jr. et al. |
| 5,413,999 A | 5/1995 | Vacca et al. |
| 5,476,874 A | 12/1995 | Hungate et al. |
| 5,502,060 A | 3/1996 | Thompson et al. |
| 5,578,597 A | 11/1996 | Spector et al. |
| 5,580,859 A | 12/1996 | Felgner et al. |
| 5,589,466 A | 12/1996 | Felgner et al. |
| 5,663,169 A | 9/1997 | Young et al. |
| 5,679,647 A | 10/1997 | Carson et al. |
| 5,703,055 A | 12/1997 | Felgner et al. |
| 5,714,374 A | 2/1998 | Arnold et al. |
| 5,736,524 A | 4/1998 | Content et al. |
| 5,739,118 A | 4/1998 | Carrano et al. |
| 5,804,566 A | 9/1998 | Carson et al. |
| 5,846,978 A | 12/1998 | Coburn et al. |
| 5,863,542 A | 1/1999 | Paoletti et al. |
| 5,922,687 A | 7/1999 | Mann et al. |

FOREIGN PATENT DOCUMENTS

| | | |
|---|---|---|
| WO | WO-98/04720 A1 | 2/1998 |
| WO | WO-98/56919 A2 | 12/1998 |
| WO | WO-01/82964 A1 | 11/2001 |

OTHER PUBLICATIONS

Riffkin et al. "A single amino-acid change between the antigenically different extracellular serine proteases V2 and B2 from *Dichelobacter nodosus*", Gene, vol. 167 (1995), pp. 279-283.*

Abaza et al. "Effects of amino acid substitutions outside an antigenic site on protein binding to monoclonal antibodies of predetermined specificity obtained by peptide immunization", Journal of Protein Chemistry, vol. 11, No. 5 (1992), pp 433-444.*

Cruse et al. Illustrated Dictionary of Immunology (Boca Raton, FL, CRC Press, Inc., 1995), p. 309. QR180.4.C78.*

Paul, Fundamental Immunology, (Philadelphia & New York, Lippincott-Raven Publishers, 1993), pp. 250 and 1311-1312. QR181. F84.*

Cohen et al. APronounced acute immunosuppression in vivo mediated by HIV Tat challenge@, Proceedings of the National Academy of Sciences of the United States of America, vol. 96, Issue 19(Sep. 14, 1999), pp. 10842☐10847.*

(Continued)

*Primary Examiner*—Jeffrey Stucker
(74) *Attorney, Agent, or Firm*—Schwegman, Lundberg, Woessner & Kluth, P.A.

(57) ABSTRACT

This invention relates to improved methods of inducing an immune response for the prevention or treatment of HIV-1 infection by using a nucleic acid vaccine in conjunction with a recombinant viral vaccine, e.g., a poxvirus vaccine, to potentiate and broaden the immune response. The present invention further provides a particularly effective vaccine regimen comprising a DNA vaccine used in combination with a poxvirus virus, especially NYVAC or ALVAC.

14 Claims, 13 Drawing Sheets

OTHER PUBLICATIONS

Mooij et al. "Rational development of prophylactic HIV vaccines based on structural and regulatory proteins" Vaccine, vol. 20, Issues 3-4, (Nov. 12, 2001) pp. 304-321.*

Kohler et al."No hope for an AIDS vaccine soon" AIDScience vol. 2, No. 5 (Mar. 2002), 3 pages, no page Nos.*

*PCT International Search Report in related application PCT/US 01/13968*, (Oct. 6, 2001),6 Pages.

"Results from EV01 HIV Vaccine Trial, London and Lausanne, Jun. 7th, 2004", (EuroVac Press Release),(Jun., 2004),2 Pages.

Abimiku, A. G., et al., "Long-Term Survival of SIV$_{Mac251}$—Infected Macaques Previously Immunized with NYVAC-SIV Vaccines", *Journal of Acquired Immune Deficiency Syndromes and Human Retrovirology, 15 (Supp 1)*, (1997),S78-S85.

AIDS Vaccine Advocacy Coalition, "Support for the RV144 HIV vaccine trial", *Science, 305(5681)*, (Jul. 9, 2004),177-80 Belshe et al.

Altman, J. D., et al., "Formation of Functional Peptide Complexes of Class II Major Histocompatibility Complex Proteins From Subunits Produced in *Escherichia coli*", *Pro. Natl. Acad. Sci. USA, 90*, (1993), 10330-10334.

Altman, J. D., et al., "Phenotypic Analysis of Antigen-Specific T Lymphocytes", *Science, 274*, (1996),94-96.

Arp, J., et al., "Human Immunodeficiency Virus Type 1 Envelope-Specific Cytotox T Lymphocytes Response Dynamics After Prime-Boost Vaccine Regimens With Human Immunodeficiency Virus Type 1 CanaryPox and Pseudovirions", *Viral Immunology, 12(4)*, (Abstract Only),(1999),1 Page.

Barnett, S. W., et al., "Prime-Boost Immunization Strategies against HIV", *AIDS Research and Human Retroviruses, 14, Supp. 3*, (1998),S-299-S-309.

Benson, J., et al., "Recombinant Vaccine-Induced Protection Against the Highly Pathogenic Simian Immunodeficiency Virus SIV$_{mac251}$: Dependence on Route of Challenge Exposure", *Journal of Virology, 72(5)*, (1998),4170-4182.

Burton, D R., et al., "Public Health. A Sound Rationale Needed for Phase III HIV-1 Vaccine Trials", *Science, 303(5656)*, (2004), 316.

Carpenter, C., et al., "Report of the NIH Panel to Define Principles of Therary of HIV Infection", *Morbidity and Mortality Weekly Report, 47 (RR-5)*, (Apr. 24, 1998),1-41.

Carroll, M. W., et al., "Host Range and Cytopathogenicity of the Highly Attenuated MVA Strain of Vaccinia Virus: Propagation and Generation of Recombinant Viruses in a Nonhuman Mammalian Cell Line", *Virology, 238(2)*, (1997),198-211.

Donnelly, J. J., et al., "DNA Vaccines", *Annu. Rev. Immunol., 15*, (1997),617-648.

Dunbar, P. R., et al., "Direct Isolation, Phenotyping and Cloning of Low-Frequency Antigen-Specific Cytotoxic T Lymphocytes from Peripheral Blood", *Current Biology, 8*, (1998),413-416.

Eloit, M., et al., "Construction of a Defective Adenovirus Vector Expressing the Pseudorabies Virus Glycoprotein gp50 and its Use as a Live Vaccine", *Journal of General Virology, 71*, (1990),2425-2431.

Felgner, P. L., et al., "Lipofection: A Highly Efficient, Lipid-Mediated DNA-Transfection Procedure", *Proc. Natl. Acad. Sci., USA*, vol. 84, (1987),7413-7417.

Fuller, D. H., et al., "Enhancement of immunodeficiency virus-specific immune responses in DNA-immunized rhesus macaques", *Vaccine, 15(8)*, (1997),924-926.

Girard, M., et al., "New prospects for the development of a vaccine against human immunodeficiency virus type 1. An overview", *C. R. Acad. Sci. Paris de la vie/Life Sciences, 322*, (1999),959-966.

Girard, M., et al., "New Prospects for the Development of a Vaccine Against Human Immunodeficiency Virus Type 1. An Overview", *C. R. Acad. Sci. Paris, Sciences de la vie / Life Sciences, 322*, (1999),959-966.

Hanke, T., et al., "Effective Induction of HIV-Specific CTL by Multi-Epitope Using Gene Gun in a Combined Vaccination Regime", *Vaccine, 17(6)*, (1999),589-596.

Hanke, T., et al., "Effective Induction of Simian Immunodeficiency Virus-Specific Cytotoxic T Lymphoctyes in Macaques by Using a Multiepitope Gene and DNA Prime-Modified Vaccinia Virus Ankara Boost Vaccination Regimen", *Journal of Virology, 73(9)*, (1999),7524-7532.

Hanke, T., et al., "Enhancement of MHC class I-restricted peptide-specific T cell induction by a DNA prime/MVA boost vaccination regime", *Vaccine, 16(5)*, (1998),439-445.

Hanke, T., et al., "Pre-clinical development of a multi-CTL epitope-based DNA prime MVA boost vaccine for AIDS", *Immunology Letters, 66*, (1999),177-181.

Kent, S. J., et al., "Enchanced T-Cell Immunogenicity and Protective Efficacy of a Human Immunodeficiency Virus Type 1 Vaccine Regimen Consisting of Consecutive Priming with DNA and Boosting with Recombinant Fowlpox Virus", *Journal of Virology, 72(12)*, (1998),10180-10188.

Lalvani, A., et al., "Rapid Effector Function in CD8+ Memory T Cells", *J. Exp. Med., 186(6)*, (1997),859-869.

Lu, S., et al., "Simian Immunodeficiency Virus DNA Vaccine Trial in Macaques", *Journal of Virology, 70(6)*, (1996),3978-3991.

Mäkitalo, B, et al., "Enhanced cellular immunity and systemic control of SHIV infection by combined parenteral and mucosal administration of a DNA prime MVA boost vaccine regimen", *J. Gen Virol., 85(Pt 8)*, (Aug. 2004),2407-19.

McNeil, J G., et al., "Policy rebuttal. HIV vaccine trial justified", *Science, 303(5660)*, (Feb. 13, 2004),961.

Murali-Krishna, K., et al., "Counting Antigen-Specific CD8 T Cells: A Reevaluation of Bystander Activation During Viral Infection", *Immunity, 8*, (1998),177-187.

Myagkikh, M., et al., "Multiple Immunizations with Attenuated Poxvirus HIV Type 2 Recombinants and Subunit Boosts Required for Protection of Rhesus Macaques", *AIDS Research and Human Retroviruses, 12(11)*, (1996),985-992.

Nicholson, J. K., "1997 Revised Guidelines for Performing CD4+ T-Cell Determinations in Persons Infected with Human Immunodeficiency Virus (HIV)", *Morbidity and Mortality Weekly Report—Recommendations and Reports, 46, No. RR-2*, (Jan. 10, 1997),1-29.

Pal, R., et al., "ALVAC-SIV-gag-pol-env-Based Vaccination and Macaque Major Histocompatibility Complex Class I (A*01) Delay Simian Immunodeficiency Virus SIV$_{mac}$-Induced Immunodeficiency", *Journal of Virology, 76(1)*, (2002),292-302.

Panicali, D., et al., "Construction of Live Vaccines by Using Genetically Engineered Poxviruses: Biological Activity of Recombinant Vaccinia Virus Expressing Influenza Virus Hemagglutinin", *Proc. Natl. Acad. Sci. USA, vol. 80*, (1983),5364-5368.

Patterson, L. J., "Cross-protection in NYVAC-HIV-1-Immunized/HIV-2-Challenged but not in NYVAC-HIV-2-Immunied/SHIV-Challenged Rhesus Macaques", *AIDS, 14(16)*, (2000),2445-2455.

Paul, W. E., *Fundamental Immunology*, (Third Edition, 1993, Raven Press),822-826.

Piccini, A., et al., "[34] Vaccinia Virus as an Expression Vector", *Methods in Enzymology, 153—Recombinant DNA, Part D*, (1987),545-563.

Ramshaw, I. A., et al., "The Prime-Boost Strategy: Exciting Prospects for Improved Vaccination", *Immunology Today, 21(4)*, (2000),163-165.

Robinson, H. L., et al., "AIDS Vaccines: Heterologous Prime/Boost Strategies for Raising Protective T Cell Responses", *AIDS Rev, 2*, (2000), 105-110.

Robinson, H. L., et al., "Neutralizing antibody-independent containment of immunodeficiency virus challenges by DNA priming and recombinant pox virus booster immunizations", *Nature Medicine, 5(5)*, (1999),526-534.

Samulski, R. J., et al., "A Recombinant Plasmid from Which an Infectious Adeno-Associated Virus Genome Can Be Excised In Vitro and Its Use to Study Viral Replication", *Journal of Virology, 61(10)*, (1987),3096-3101.

Samulski, R. J., et al., "Helper-Free Stocks of Recombinant Adeno-Associated Viruses: Normal Integration Does Not Require Viral Gene Expression", *Journal of Virology, 63(9)*, (1989),3822-3828.

Schneider, J., et al., "Enhanced Immunogenicity for CD8+ T Cell Induction and Complete Protective Efficacy of Malaria DNA Vaccination by Boosting with Modified Vaccinia Virus Ankara", *Nature Medicine, 4(4)*, (1998),397-402.

Sedegah, M., et al., "Boosting with recombinant vaccinia increases immunogenicity and protective efficacy of malaria DNA vaccine", *Proc. Natl. Acad. Sci. USA, 95*, (1998),7648-7653.

Szoka, F., et al., "Comparative Properties and Methods of Preparation of Lipid Vesicles (Liposomes)", *Ann. Rev. Biophy. Bioeng., 9*, (1980),467-508.

Wang, S W., et al., "An SHIV DNA/MVA rectal vaccination in macaques provides systemic and mucosal virus-specific responses and protection against AIDS", *AIDS Res Hum Retroviruses, 20(8)*, (Aug. 2004),846-59.

Wolff, J. A., et al., "Direct Gene Transfer into Mouse Muscle in Vivo", *Science, 247*, (1990),1465-1468.

AIDS International Ltd., "HIV gp120 vaccine—VaxGen: AIDSVAX, AIDSVAX B/B, AIDSVAX B/E, HIV gp120 vaccine—Genentech, HIV gp120 vaccine AIDSVAX—VaxGen, HIV vaccine AIDSVAX—VaxGen.", *Drugs R. D., 4(4)*, (2003), 249-53.

Amara, Rama R., et al., "Control of a Mucosal Challenge and Prevention of AIDS by a Multiprotein DNA/MVA Vaccine", *SCIENCE, vol. 292*, (Apr. 6, 2001), 69-74.

Amara, R R., "Studies on the cross-clade and cross-species conservation of HIV-1 Gag-specific CD8 and CD4 T cell responses elicited by a clade B DNA/MVA vaccine in macaques", *Virology, 334 (1)*, (Mar. 30, 2005), 124-33.

Bayes, M, "Gateways to clinical trials", *Methods Find Exp Clin Pharmacol., 26(4)*, (May 2004), 295-318.

Berzofsky, Jay A., et al., "Progress on new vaccine strategies against chronic viral infections", *The Journal of Clinical Investigation, vol. 114, No. 4*, (Aug. 2004), 450-462.

Bolesta, E., "Clustered epitopes within the Gag-Pol fusion protein DNA vaccine enhance immune responses and protection against challenge with recombinant vaccinia viruses expressing HIV-1 Gag and Pol antigens", *Virology, 332(2)*, (Feb. 20, 2005), 467-79.

Boyer, Jean D., et al., "Vaccination of Seronegative Volunteers with a Human Immunodeficiency Virus Type 1 *envirev* DNA Vaccine Induces Antigen-Specific Proliferation and Lymphocyte Production of β-Chemokines", *The Journal of Infectious Diseases, vol. 181*, (2000), 476-483.

Jaoko, W. G., et al., "Safety profile of DNA and MVA HIV preventive vaccines", http://www.iasociety.org/abstract/show.asp?abstract id=2170484, (observed Sep. 27, 2004), 2 Pages.

Jin, Xia, "Safety and Immunogenicity of ALVAC vCP1452 and Recombinant gp160 in Newly Human Immunodeficiency Virus Type 1-Infected Patients Treated with Prolonged Highly Active Antiretroviral Therapy", *Journal of Virology*, vol. 76, No. 5, (Mar. 2002), 2206-2216.

Lee, D., "Breakthrough infections during phase 1 and 2 prime-boost HIV-1 vaccine trials with canarypox vectors (ALVAC) and booster dose of recombinant gp120 or gp160", *J. Infect Dis., 190(5)*, Epub 2004 Jul. 29, (Sep. 1, 2004), 903-7.

Montefiori, D. C., "Demographic factors that influence the neutralizing antibody response in recipients of recombinant HIV-1 gp120 vaccines", *J. Infect Dis., 190(11)*, Epub 2004 Oct. 28, (Dec. 1, 2004), 1962-9.

Perrin, L., "Therapeutic vaccination in primary HIV infection, the Quest trial", *Vaccine, 20(15)*, (May 6, 2002), 2004-2006.

Sadagopal, S., "Signature for long-term vaccine-mediated control of a Simian and human immunodeficiency virus 89.6P challenge: stable low-breadth and low-frequency T-cell response capable of coproducing gamma interferon and interleukin-2", *Journal of Virology, 79(6)*, (Mar. 2005), 3243-53.

Singh, D. K., "A noninfectious simian/human immunodeficiency virus DNA vaccine that protects macaques against AIDS", *Journal of Virology, 79(6)*, (Mar. 2005), 3419-28.

Smith, J. M., "DNA/MVA vaccine for HIV type 1: effects of codon-optimization and the expression of aggregates or virus-like particles on the immunogenicity of the DNA prime", *AIDS Res Hum Retroviruses, 20(12)*, (Dec. 2004), 1335-47.

Smith, J. M., "Studies in macaques on cross-clade T cell responses elicited by a DNA/MVA AIDS vaccine, better conservation of CD8 than CD4 T cell responses", *AIDS Res Hum Retroviruses, 21(2)*, (Feb. 2005), 140-144.

Okuda et al. Vaccine, vol. 15, No. 10 (1997), pp. 1049-1056.*

"Animal Models", *The NIAID Division of AIDS, Science,* http://www.niaid.nih.gov/daids/vaccine/animals.htm, (Archived Jan. 23, 2000), 2 pages.

* cited by examiner

IMMUNOGENICITY USING A COMBINATION OF DNA AND VACCINIA VIRUS VECTOR VACCINES

CROSS-REFERENCE TO RELATED APPLICATIONS

The present application claims the benefit of priority of U.S. Provisional Application 60/200,444 filed Apr. 28, 2000, which is herein incorporated by reference.

STATEMENT AS TO RIGHTS TO INVENTIONS MADE UNDER FEDERALLY SPONSORED RESEARCH AND DEVELOPMENT

[Not Applicable]

FIELD OF THE INVENTION

This invention relates to improved methods of inducing an immune response for the prevention or treatment of human immunodeficiency virus-1 (HIV-1) infection by using a nucleic acid vaccine in conjunction with a recombinant viral vaccine, e.g., a poxvirus vaccine, to potentiate and broaden the immune response. The present invention further provides a particularly effective vaccine regimen comprising a DNA vaccine used in combination with a recombinant poxvirus virus, especially NYVAC or ALVAC.

SUMMARY OF THE INVENTION

The present invention is directed to a method of stimulating an immune response in a human at risk for infection, or infected with, an HIV-1 retrovirus. The method comprises administering a first vaccine, frequently a nucleic acid vaccine, which enters the cells and intracellularly produces HIV-specific peptides for presentation on the cell's MHC class I molecules in an amount sufficient to stimulate a CD8$^+$ immune response. The first vaccine may be used in combination with a second vaccine comprising another modality, e.g., a recombinant pox virus vector. The use of the combination of vaccines potentiates the immune response relative to the use of either of the vaccines alone.

The vaccine combination may be administered prophylactically to individuals at risk of HIV infection. To prevent infection, individuals who are non vaccinia-naïve may particularly benefit. Alternatively, patients already infected with HIV may receive the vaccine regimen therapeutically. Patients who are candidates for treatment with the vaccine regimen of the invention include those who have a viral load of less than 10,000 viral copies per ml of plasma and a CD4$^+$ cell count of above 500 cells/ml. Other patients include those who have been treated with one or more anti-viral agents.

The method frequently employs a nucleic acid vaccine that is a DNA vaccine in combination with an attenuated recombinant virus. A preferred virus is an attenuated pox virus, particularly NYVAC and ALVAC, attenuated vaccinia and canarypox viruses respectively. The DNA vaccine and/or the recombinant virus vaccine may be administered one or more times. The DNA vaccine is preferably administered prior to administration of the recombinant virus vaccine, frequently in multiple doses. In one embodiment, a DNA vaccine encoding various HIV antigens, or epitopes derived from the antigens, is administered multiple times prior to administration of a NYVAC-HIV vaccine.

The vaccine may also comprise interleukin-2 (IL-2) or CD40 ligand in an amount that is sufficient to further potentiate the CD8$^+$ and CD4$^+$ T-cell responses.

BRIEF DESCRIPTION OF THE FIGURES

FIG. 1 shows the study design evaluating a combination DNA vaccine/NYVAC vaccine in *Rhesus macaques*. Three groups of 8 rhesus macaques each were included. The animals were immunized four times with either mock NYVAC (group A) or NYVAC-SIV-gag-pol-env (group B), or three times with DNA-SIV-gag-env followed by two immunizations with NYVAC-SW-gag-pol-env at the times indicated.

FIG. 2 shows lymphoproliferative responses to gp120 (upper panel) and p27 antigens (lower panel) in the three groups inoculated in accordance with the study design set forth in FIG. 1.

FIG. 3 shows the frequency of Gag181-specific CD8$^+$ T-cells in peripheral blood monocytes (PBMC) of vaccinated macaques as measured by IFN-γ ELISPOT assay at the times indicated. "S.F.C." indicates spot-forming cells/per million; "N.D." indicates not done. An asterisk above the bar marks the values obtained by assaying frozen cells.

FIG. 4 shows Gag181-specific tetramer staining of fresh PBMC at week 53 and 76. The cells depicted in the Figure were first gated for CD3$^+$ population.

FIG. 5 shows the T-cell responses to various SIV epitopes measured using ELISPOT and $^{51}$Cr-release assays.

FIG. 6 shows the average group viremia during the first 28 days following intrarectal challenge with SIV-mac251. Points represent group means with standard error indicated by the bar.

FIG. 7 shows the average value of Gag181 tetramer-specific staining in all MAMU-A*01-positive animals in each group after challenge. Points represent the mean of the percentage of Gag181 tetramer-positive cells of the total CD3$^+$CD8$^+$ T-cell population with standard errors indicated by bars.

FIG. 8 shows the average group viremia in MAMU A*01-positive and MAMU A*01-negative animals of control and DNA/NYVAC-SIV vaccinated (group C) animals. In the control group, the results obtained in two studies were combined. Points represent group means with standard errors indicated by the bars.

DEFINITIONS

Figure 1:
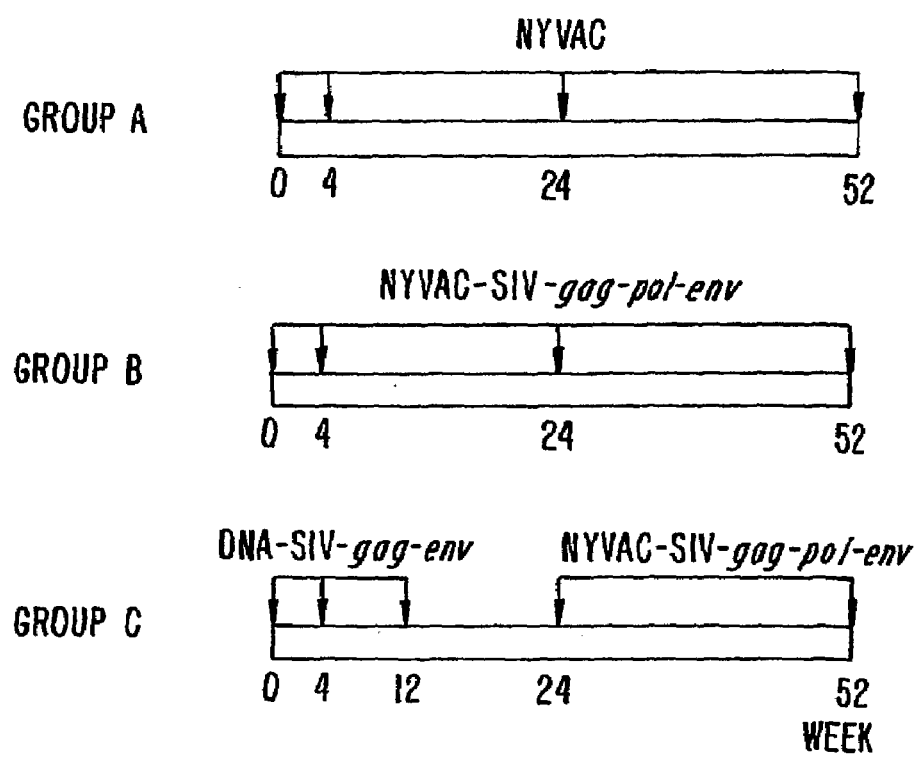
FIG. 1.

"Attenuated recombinant virus" refers to a virus that has been genetically altered by modern molecular biological methods, e.g. restriction endonuclease and ligase treatment, and rendered less virulent than wild type, typically by deletion of specific genes or by serial passage in a non-natural host cell line or at cold temperatures.

"Efficient CD8$^+$ response" is referred to as the ability of cytotoxic CD8$^+$ T-cells to recognize and kill cells expressing foreign peptides in the context of a major histocompatibility complex (MHC) class I molecule.

"Nonstructural viral proteins" are those proteins that are needed for viral production but are not necessarily found as components of the viral particle. They include DNA binding proteins and enzymes that are encoded by viral genes but which are not present in the virions. Proteins are meant to include both the intact proteins and fragments of the proteins or peptides which are recognized by the immune cell as epitopes of the native protein.

A "nucleic acid vaccine" or "naked DNA vaccine" refers to a vaccine that includes one or more expression vectors that encodes B-cell and/or T-cell epitopes and provides an immunoprotective response in the person being vaccinated. As used herein, the term does not include a recombinant pox viral vaccine.

"Plasma" refers to the fraction of whole blood resulting from low speed centrifugation of EDTA- or heparin-treated blood.

"Pox viruses" are large, enveloped viruses with double-stranded DNA that is covalently closed at the ends. Pox viruses replicate entirely in the cytoplasm, establishing discrete centers of viral synthesis. Their use as vaccines has been known since the early 1980's (see, e.g. Panicali, D. et al. "Construction of live vaccines by using genetically engineered pox viruses: biological activity of recombinant vaccinia virus expressing influenza virus hemagglutinin", Proc. Natl. Acad. Sci. USA 80:5364–5368, 1983).

"Potentiating" or "enhancing" an immune response means increasing the magnitude and/or the breadth of the immune response, i.e., the number of cells induced by a particular epitope may be increased and/or the numbers of epitopes that are recognized may be increased ("breadth"). A 5-fold, often 10-fold or greater, enhancement in both $CD8^+$ and $CD4^+$ T-cell responses is obtained with administration of a combination of nucleic acid/recombinant virus vaccines compared to administration of either vaccine alone.

A "retrovirus" is a virus containing an RNA genome and an enzyme, reverse transcriptase, which is an RNA-dependent DNA polymerase that uses an RNA molecule as a template for the synthesis of a complementary DNA strand. The DNA form of a retrovirus commonly integrates into the host-cell chromosomes and remains part of the host cell genome for the rest of the cell's life.

"Structural viral proteins" are those proteins that are physically present in the virus. They include the capsid proteins and enzymes that are loaded into the capsid with the genetic material. Because these proteins are exposed to the immune system in high concentrations, they are considered to be the proteins most likely to provide an antigenic and immunogenic response. Proteins are meant to include both the intact proteins and fragments of the proteins or peptides which are recognized by the immune cell as epitopes of the native protein.

"Viral load" is the amount of virus present in the blood of a patient. Viral load is also referred to as viral titer or viremia. Viral load can be measured in variety of standard ways. In preferred embodiments, the DNA/recombinant virus prime boost protocol of the invention controls viremia and leads to a greater reduction in viral load than that obtained when either vaccine is used alone.

DETAILED DESCRIPTION

Introduction

Recombinant pox viruses vaccines, e.g., NYVAC- and ALVAC-based vaccines for HIV-1 have been tested in preclinical trials using either HIV-2 or SIV Gag, Pol, and Env genes in macaques (see, e.g., Benson et al., J. Virol. 72:4170–4182, 1998; Abimiku et al., J. Acquir. Immune Defic. Synd. Hum. Retrovirol. 15:S78–S85, 1997; Myagkikh et al., AIDS Res. Hum. Retroviruses 12:985–991, 1996; and Hel et al., Nat. Med. 16:1140–1146, 2000). Results from these early studies indicated that, while these vaccines do not protect from infection, they significantly reduce the viral replication within a few weeks from exposure in approximately 50% of the animals. In the case of NYVAC-SIV vaccination, the regimen changed the natural course of $SIV_{251}$ infection.

In the macaque animal model, the addition of monomeric gp120 protein administered as a boost in conjunction with ALVAC-SIV gpe did not appear to improve the level of protection. (see, e.g., Pal et al., Abstract for "HIV/AIDS Vaccine Development Workshop," Paris, France, May 5–6, 2000). These studies also suggested that more than three immunizations with NYVAC-SIV/ALVAC-SIV may not further increase the pool of memory cells, and that the vector immunity against vaccinia protein may blunt the response to SIV antigens.

Various other prime boost immunization strategies against HIV have also been proposed (see, e.g., Barnett et al., AIDS Res. and Human Retroviruses Volume 14, Supplement 3, 1998, pp. S-299–S-309 and Girard et al., C R Acad. Sci III 322:959–966, 1999 for reviews). DNA immunization, when used in a boosting protocol with modified vaccinia virus Ankara (MVA) or with a recombinant fowl pox virus (rFPV) in the macaque model, has been shown to induce CTL responses and antibody responses (see, e.g., Hanke et al, J. Virol. 73:7524–7532, 1999; Hanke et al., Immunol. Letters 66:177–181; Robinson et al., Nat. Med. 5:526–534, 1999), but no protection from a viral challenge was achieved in the immunized animals. DNA immunization followed by administration of another highly attenuated poxvirus has also been tested for the ability to elicit IgG responses, but the interpretation of the results is hampered by the fact that serial challenges were performed (see, e.g., Fuller et al., Vaccine 15:924–926, 1997; Barnett et al., supra). In contrast, in a murine model of malaria, DNA vaccination used in conjunction with a recombinant vaccinia virus was promising in protecting from malaria infection (see, e.g., Sedegah et al., Proc. Natl. Acad. Sci. USA 95:7648–7653, 1998; Schneider et al., Nat. Med. 4:397–402, 1998).

The present invention provides for enhanced immunogenicity of a recombinant poxvirus-based vaccine by administering a nucleic acid, e.g., a DNA vaccine, to stimulate an immune response to the HIV antigens provided in the poxvirus vaccine, and thereby increase the ability of the recombinant pox virus, e.g., NYVAC or ALVAC, to expand a population of immune cells.

Individuals who are treated with the vaccine regimen may be at risk for infection with the virus or may have already been infected.

Vaccines of Use in This Invention

Vaccines useful for the induction of $CD8^+$ T-cell responses comprise nucleic acid vaccines (preferably delivered as a DNA vaccine) and recombinant pox virus vaccines that provide for the intracellular production of viral-specific peptide epitopes that are presented on MHC Class I molecules and subsequently induce an immunoprotective cytotoxic T lymphocyte (CTL) response.

The invention contemplates single or multiple administrations of the nucleic acid vaccine in combination with one or more administrations of the recombinant virus vaccine. This vaccination regimen may be complemented with administration of recombinant protein vaccines, or may be used with additional vaccine vehicles. Preferably, administration of the nucleic acid vaccine precedes administration of the recombinant virus vaccine.

In preferred embodiments, the DNA/recombinant virus prime boost protocol controls viremia and reduces viral load as well as potentiating a $CD8^+$ response.

Attenuated Recombinant Viral Vaccines

Attenuated recombinant poxviruses that express retrovirus-specific epitopes are of use in this invention. Attenuated viruses are modified from their wildtype virulent form to be either symptomless or weakened when infecting humans. Typically, the genome of the virus is defective in respect of a gene essential for the efficient production or essential for the production of infectious virus. The mutant virus acts as a vector for an immunogenic retroviral protein by virtue of the virus encoding foreign DNA. This provokes or stimulates a cell-mediated $CD8^+$ response.

The virus is then introduced into a human vaccinee by standard methods for vaccination of live vaccines. A live vaccine of the invention can be administered at, for example, about $10^4$–$10^8$ organisms/dose, or $10^6$ to $10^9$ pfu per dose. Actual dosages of such a vaccine can be readily determined by one of ordinary skill in the field of vaccine technology.

The poxviruses are of preferred use in this invention. There are a variety of attenuated poxviruses that are available for use as a vaccine against HIV. These include attenuated vaccinia virus, cowpox virus and canarypox virus. In brief, the basic technique of inserting foreign genes into live infectious poxvirus involves a recombination between pox DNA sequences flanking a foreign genetic element in a donor plasmid and a homologous sequences present in the rescuing poxvirus as described in Piccini et al., Methods in Enzymology 153, 545–563 (1987). More specifically, the recombinant poxviruses are constructed in two steps known in the art and analogous to the methods for creating synthetic recombinants of poxviruses such as the vaccinia virus and avipox virus described in U.S. Pat. Nos. 4,769,330, 4,722,848, 4,603,112, 5,110,587, and 5,174,993, the disclosures of which are incorporated herein by reference.

First, the DNA gene sequence encoding an antigenic sequence such as a known T-cell epitope is selected to be inserted into the virus and is placed into an E. coli plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within E. coli bacteria.

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences.

Attenuated recombinant pox viruses are a preferred vaccine. A detailed review of this technology is found in U.S. Pat. No. 5,863,542, which is incorporated by reference herein. These viruses are modified recombinant viruses having inactivated virus-encoded genetic functions so that the recombinant virus has attenuated virulence and enhanced safety. The functions can be non-essential, or associated with virulence. The poxvirus is generally a vaccinia virus or an avipox virus, such as fowlpox virus and canarypox virus. The viruses are generated using the general strategy outlined above and in U.S. Pat. No. 5,863,542.

Representative examples of recombinant pox viruses include ALVAC, TROVAC, NYVAC, and vCP205 (ALVAC-MN120TMG). These viruses were deposited under the terms of the Budapest Treaty with the American Type Culture Collection (ATCC), 12301 Parklawn Drive, Rockville, Md., 20852, USA: NYVAC under ATCC accession number VR-2559 on Mar. 6, 1997; vCP205 (ALVAC-MN120TMG) under ATCC accession number VR-2557 on Mar. 6, 1997; TROVAC under ATCC accession number VR-2553 on Feb. 6, 1997 and, ALVAC under ATCC accession number VR-2547 on Nov. 14, 1996.

NYVAC is a genetically engineered vaccinia virus strain generated by the specific deletion of eighteen open reading frames encoding gene products associated with virulence and host range. NYVAC is highly attenuated by a number of criteria including: i) decreased virulence after intracerebral inoculation in newborn mice, ii) inocuity in genetically ($nu^+/nu^+$) or chemically (cyclophosphamide) immunocompromised mice, iii) failure to cause disseminated infection in immunocompromised mice, iv) lack of significant induration and ulceration on rabbit skin, v) rapid clearance from the site of inoculation, and vi) greatly reduced replication competency on a number of tissue culture cell lines including those of human origin.

TROVAC refers to an attenuated fowlpox that was a plaque-cloned isolate derived from the FP-1 vaccine strain of fowlpoxvirus which is licensed for vaccination of 1 day old chicks.

ALVAC is an attenuated canarypox virus-based vector that was a plaque-cloned derivative of the licensed canarypox vaccine, Kanapox (Tartaglia et al., 1992). ALVAC has some general properties which are the same as some general properties of Kanapox. ALVAC-based recombinant viruses expressing extrinsic immunogens have also been demonstrated efficacious as vaccine vectors. This avipox vector is restricted to avian species for productive replication. On human cell cultures, canarypox virus replication is aborted early in the viral replication cycle prior to viral DNA synthesis. Nevertheless, when engineered to express extrinsic immunogens, authentic expression and processing is observed in vitro in mammalian cells and inoculation into numerous mammalian species induces antibody and cellular immune responses to the extrinsic immunogen and provides protection against challenge with the cognate pathogen.

NYVAC, ALVAC and TROVAC have also been recognized as unique among all poxviruses in that the National Institutes of Health ("NIH")(U.S. Public Health Service), Recombinant DNA Advisory Committee, which issues guidelines for the physical containment of genetic material such as viruses and vectors, i.e., guidelines for safety procedures for the use of such viruses and vectors which are based upon the pathogenicity of the particular virus or vector, granted a reduction in physical containment level: from BSL2 to BSL1. No other poxvirus has a BSL1 physical containment level. Even the Copenhagen strain of vaccinia virus-the common smallpox vaccine-has a higher physical containment level; namely, BSL2. Accordingly, the art has recognized that NYVAC, ALVAC and TROVAC have a lower pathogenicity than any other poxvirus.

Another attenuated poxvirus of preferred use for this invention is Modified Vaccinia virus Ankara (MVA), which acquired defects in its replication ability in humans as well as most mammalian cells following over 500 serial passages in chicken fibroblasts (see, e.g., Mayr et al., *Infection* 3:6–14 (1975); Carrol, M. and Moss, B. *Virology* 238:198–211 (1997)). MVA retains its original immunogenicity and its variola-protective effect and no longer has any virulence and contagiousness for animals and humans. As in the case of NYVAC or ALVAC, expression of recombinant protein occurs during an abortive infection of human cells, thus providing a safe, yet effective, delivery system for foreign antigens.

The HIV antigen-encoding DNA for insertion into these vectors are any that are known to be effective antigens for protection against a retrovirus. These can include both structural and non-structural proteins. The envelope, polymerase, gag, and protease are preferred proteins or sources of epitopes, but other proteins or epitopes can also be employed including those proteins encoded by non-structural genes, e.g., rev, tat, nef, vif and vpr. For HIV, nucleic acids that can be inserted into the viral vector includes, but are not limited to, nucleic acid that can code for at least one of: HIV1gag(+pro)(IIIB), gp120(MN)(+transmembrane), nef(BRU)CTL, pol(IIIB)CTL, ELDKWA or LDKW epitopes, preferably HIV1gag(+pro)(IIIB), gp120(MN) (+transmembrane), two (2) nef(BRU)CTL and three (3) pol(IIIB)CTL epitopes; or two ELDKWA in gp120 V3 or another region or in gp160. The two (2) nef(BRU)CTL and three (3) pol(IIIB)CTL epitopes are preferably CTL1, CTL2, pol1, pol2 and pol3. In the above listing, the viral strains from which the antigens are derived are noted parenthetically.

Nucleic Acid Vaccines

The vaccine combination of the invention typically includes as one of the vaccines a nucleic acid vaccine, preferably DNA. Nucleic acid vaccines as defined herein, typically plasmid expression vectors, are not encapsidated in a viral particle. The nucleic acid vaccine is directly introduced into the cells of the individual receiving the vaccine regimen. This approach is described, for instance, in Wolff et. al., Science 247:1465 (1990) as well as U.S. Pat. Nos. 5,580,859; 5,589,466; 5,804,566; 5,739,118; 5,736,524; 5,679,647; and WO 98/04720. Examples of DNA-based delivery technologies include, "naked DNA", facilitated (bupivicaine, polymers, peptide-mediated) delivery, and cationic lipid complexes or liposomes. The nucleic acids can be administered using ballistic delivery as described, for instance, in U.S. Pat. No. 5,204,253 or pressure (see, e.g., U.S. Pat. No. 5,922,687). Using this technique, particles comprised solely of DNA are administered, or in an alternative embodiment, the DNA can be adhered to particles, such as gold particles, for administration.

As is well known in the art, a large number of factors can influence the efficiency of expression of antigen genes and/or the immunogenicity of DNA vaccines. Examples of such factors include the reproducibility of inoculation, construction of the plasmid vector, choice of the promoter used to drive antigen gene expression and stability of the inserted gene in the plasmid.

Any of the conventional vectors used for expression in eukaryotic cells may be used for directly introducing DNA into tissue. Expression vectors containing regulatory elements from eukaryotic viruses are typically used in eukaryotic expression vectors, e.g., SV40 CMB vectors. Other exemplary eukaryotic vectors include pMSG, pAV009/A+, pMTO10/A+, pMAMneo-5, and any other vector allowing expression of proteins under the direction of such promoters as the SV40 early promoter, SV40 later promoter, metallothionein promoter, human cytomegalovirus promoter, murine mammary tumor virus promoter, Rous sarcoma virus promoter, polyhedrin promoter, or other promoters shown effective for expression in eukaryotic cells.

Therapeutic quantities of plasmid DNA can be produced for example, by fermentation in E. coli, followed by purification. Aliquots from the working cell bank are used to inoculate growth medium, and grown to saturation in shaker flasks or a bioreactor according to well known techniques. Plasmid DNA can be purified using standard bioseparation technologies such as solid phase anion-exchange resins. If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is particularly suitable for intramuscular (IM) or intradermal (ID) administration.

To maximize the immunotherapeutic effects of minigene DNA vaccines, alternative methods for formulating purified plasmid DNA may be desirable. A variety of methods have been described, and new techniques may become available. Cationic lipids can also be used in the formulation (see, e.g., as described by WO 93/24640; Mannino & Gould-Fogerite, BioTechniques 6(7): 682 (1988); U.S. Pat. No. 5,279,833; WO 91/06309; and Felgner, et al., Proc. Nat'l Acad. Sci. USA 84:7413 (1987). In addition, glycolipids, fusogenic liposomes, peptides and compounds referred to collectively as protective, interactive, non-condensing compounds (PINC) could also be complexed to purified plasmid DNA to influence variables such as stability, intramuscular dispersion, or trafficking to specific organs or cell types.

Selection of an HIV Specific Epitope.

Highly antigenic proteins or epitopes for provoking an immune response selective for a specific retroviral pathogen are known. Typically, HIV is the target retroviral pathogen. With minor exceptions, the following discussion of HIV epitopes is applicable to other retroviruses except for the differences in sizes of the respective viral proteins. Nucleic acids for inclusion in the expression constructs can can include sequences encoding either structural or non-structural proteins or epitopes corresponding to regions of the proteins. The envelope, gag, and protease genes are preferred proteins or sources of epitopes for inclusion in the nucleic acid expression vector, but other proteins can also be used. Non-structural genes include the rev, tat, nef, vif, and vpr genes and these may also be included as components of the nucleic acid vaccines used in the invention.

Characterization of the Immune Response in Vaccinated Individuals

The vaccine regimen can be delivered to individuals at risk for infection with HIV or to patients who are infected with the virus. In order to assess the efficacy of the vaccine, the immune response can be assessed by measuring the induction of $CD4^+$, $CD8^+$, and antibody responses to particular epitopes. Moreover, viral titer can be measured in patients treated with the vaccine who are already infected. These parameters can be measured using techniques well known to those of skill in the art. Examples of such techniques are described below.

$CD4^+$ T Cell Counts

To assess the effectiveness of the vaccine combination in a recipient and to monitor the immune system of a patient already infected with the virus who is a candidate for treatment with the vaccine regimen, it is important to measure $CD4^+$ T cell counts. A detailed description of this procedure was published by Janet K. A. Nicholson, Ph.D et al. 1997 Revised Guidelines for Performing CD4+ T-Cell Determinations in Persons Infected with Human Immunodeficiency Virus (HIV) in The Morbidity and Mortality Weekly Report, 46(RR-2):[inclusive page numbers], Feb. 14, 1997. Centers for Disease Control.

In brief, most laboratories measure absolute CD4+ T-cell levels in whole blood by a multi-platform, three-stage process. The CD4+ T-cell number is the product of three laboratory techniques: the white blood cell (WBC) count; the percentage of WBCs that are lymphocytes (differential); and the percentage of lymphocytes that are CD4+ T-cells. The last stage in the process of measuring the percentage of CD4+ T-lymphocytes in the whole-blood sample is referred to as "immunophenotyping by flow cytometry.

Immunophenotyping refers to the detection of antigenic determinants (which are unique to particular cell types) on the surface of WBCs using antigen-specific monoclonal antibodies that have been labeled with a fluorescent dye or fluorochrome (e.g., phycoerythrin [PE] or fluorescein isothiocyanate [FITC]). The fluorochrome-labeled cells are analyzed by using a flow cytometer, which categorizes individual cells according to size, granularity, fluorochrome, and intensity of fluorescence. Size and granularity, detected by light scattering, characterize the types of WBCs (i.e., granulocytes, monocytes, and lymphocytes). Fluorochrome-labeled antibodies distinguish populations and subpopulations of WBCs.

Systems for measuring CD4+ cells are commercially available. For example Becton Dickenson's FACSCount System automatically measure absolutes CD4+, CD8+, and CD3+ T lymphocytes. It is a self-contained system, incorporating instrument, reagents, and controls.

A successful increase of CD4+ cell counts would be a 2× or higher increase in the number of CD4+ cells.

Measurements of CD8+ Responses

CD8+ T-cell responses may be measured, for example, by using tetramer staining of fresh or cultured PBMC, ELISPOT assays or by using functional cytotoxicity assays, which are well-known to those of skill in the art. For example, a functional cytotoxicity assay can be performed as follows. Briefly, peripheral blood lymphocytes from patients are cultured with HIV peptide epitope at a density of about five million cells/ml. Following three days of culture, the medium is supplemented with human IL-2 at 20 units/ml and the cultures are maintained for four additional days. PBLs are centrifuged over Ficoll-Hypaque and assessed as effector cells in a standard $^{51}$Cr-release assay using U-bottomed microtiter plates containing about $10^4$ target cells with varying effector cell concentrations. All cells are assayed twice. Autologous B lymphoblastoid cell lines are used as target cells and are loaded with peptide by incubation overnight during $^{51}$Cr labeling. Specific release is calculated in the following manner: (experimental release–spontaneous release)/(maximum release–spontaneous release)×100. Spontaneous release is generally less than 20% of maximal release with detergent (2% Triton X-100) in all assays. A successful CD8+ response occurs when the induced cytolytic activity is above 10% of controls.

Another measure of CD8+ responses provides direct quantification of antigen-specific T cells by staining with Fluorescein-labeled HLA tetrameric complexes (Altman, J. D. et al., *Proc. Natl. Acad. Sci. USA* 90:10330, 1993; Altman, J. D. et al., Science 274:94, 1996). Other assays include staining for intracellular lymphokines, and γ-interferon release assays or ELISPOT assays. Tetramer staining, intracellular lymphoidne staining and ELISPOT assays all are sensitive measures of T cell response (Lalvani, A. et al., *J. Exp. Med.* 186:859, 1997; Dunbar, P. R. et al., *Curr. Biol.* 8:413, 1998; Murali-Krishna, K. et al., *Immunity* 8:177, 1998).

Viral Titer

There are a variety of ways to measure viral titer in a patient. A review of the state of this art can be found in the Report of the NIH To Define Principles of Therapy of HIV Infection as published in the; Morbidity and Mortality Weekly Reports, Apr. 24, 1998, Vol 47, No. RR-5, Revised Jun. 17, 1998. It is known that HIV replication rates in infected persons can be accurately gauged by measurement of plasma HIV concentrations.

HIV RNA in plasma is contained within circulating virus particles or virions, with each virion containing two copies of HIV genomic RNA. Plasma HIV RNA concentrations can be quantified by either target amplification methods (e.g., quantitative RT polymerase chain reaction [RT-PCR], Amplicor HIV Monitor assay, Roche Molecular Systems; or nucleic acid sequence-based amplification, [NASBA®], NucliSens™ HIV-1 QT assay, Organon Teknika) or signal amplification methods (e.g., branched DNA [bDNA], Quantiplex™ HIV RNA bDNA assay, Chiron Diagnostics). The bDNA signal amplification method amplifies the signal obtained from a captured HIV RNA target by using sequential oligonucleotide hybridization steps, whereas the RT-PCR and NASBA® assays use enzymatic methods to amplify the target HIV RNA into measurable amounts of nucleic acid product. Target HIV RNA sequences are quantitated by comparison with internal or external reference standards, depending upon the assay used.

Formulation of Vaccines and Administration

The administration procedure for recombinant virus or DNA is not critical. Vaccine compositions (e.g., compositions containing the poxvirus recombinants or DNA) can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular patient, and the route of administration.

The vaccines can be administered prophylactically or therapeutically. In prophylactic administration, the vaccines are administered in an amount sufficient to induce CD8+ and CD4+, or antibody, responses. In therapeutic applications, the vaccines are administered to a patient in an amount sufficient to elicit a therapeutic effect, i.e., a CD8+, CD4+, and/or antibody response to the HIV-1 antigens or epitopes encoded by the vaccines that cures or at least partially arrests or slows symptoms and/or complications of HIV infection. An amount adequate to accomplish this is defined as "therapeutically effective dose." Amounts effective for this use will depend on, e.g., the particular composition of the vaccine regimen administered, the manner of administration, the stage and severity of the disease, the general state of health of the patient, and the judgment of the prescribing physician.

The vaccine can be administered in any combination, the order is not critical. In some instances, for example, a DNA HIV vaccine is administered to a patient more than once followed by delivery of one or more administrations of the recombinant pox virus vaccine. The recombinant viruses are typically administered in an amount of about $10^4$ to about $10^9$ pfu per inoculation; often about $10^4$ pfu to about $10^6$ pfu. Higher dosages such as about $10^4$ pfu to about $10^{10}$ pfu, e.g., about $10^5$ pfu to about $10^9$ pfu, or about $10^6$ pfu to about $10^8$ pfu, can also be employed. For example, a NYVAC-HIV vaccine can be inoculated by the intramuscular route at a dose of about $10^8$ pfu per inoculation, for a patient of 170 pounds.

Suitable quantities of DNA vaccine, e.g., plasmid or naked DNA can be about 1 µg to about 100 mg, preferably 0.1 to 10 mg, but lower levels such as 0.1 to 2 mg or 1–10 µg can be employed. For example, an HIV DNA vaccine, e.g., naked DNA or polynucleotide in an aqueous carrier, can be injected into tissue, e.g., intramuscularly or intradermally, in amounts of from 10 µl per site to about 1 ml per site. The concentration of polynucleotide in the formulation is from about 0.1 µg/ml to about 20 mg/ml.

The vaccines may be delivered in a physiologically compatible solution such as sterile PBS in a volume of, e.g., one ml. The vaccines can also be lyophilized prior to delivery. As well known to those in the art, the dose may be proportional to weight.

The compositions included in the vaccine regimen of the invention can be co-administered or sequentially administered with other immunological, antigenic or vaccine or therapeutic compositions, including an adjuvant, a chemical or biological agent given in combination with or recombinantly fused to an antigen to enhance immunogenicity of the antigen. Additional therapeutic products can include, e.g., interleukin-2 (IL-2) or CD40 ligand in an amount that is sufficient to further potentiate the $CD8^+$ and $CD4^+$ T-cell responses. Such other compositions can also include purified antigens from the immunodeficiency virus or from the expression of such antigens by a second recombinant vector system which is able to produce additional therapeutic compositions. For examples, these compositions can include a recombinant poxvirus which expresses other immunodeficiency antigens or biological response modifiers (e.g., cytokines or co-stimulating molecules). Examples of adjuvants which also may be employed include Freund's complete adjuvant and MPL-TDM adjuvant (monophosphoryl Lipid A, synthetic trehalose dicorynomycolate). Again, co-administration is performed by taking into consideration such known factors as the age, sex, weight, and condition of the particular patient, and, the route of administration.

The viral and DNA vaccines can additionally be complexed with other components such as lipids, peptides, polypeptides and carbohydrates for delivery.

The DNA vaccines are administered by methods well known in the art as described in Donnelly et al. (*Ann. Rev. Immunol.* 15:617–648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997). The vectors can also be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

Vaccines may be delivered via a variety of routes. Typical delivery routes include parenteral administration, e.g., intradermal, intramuscular or subcutaneous delivery. Other routes include oral administration, intranasal, and intravaginal routes. For DNA vaccines in particular, the vaccines can be delivered to the interstitial spaces of tissues of an individual (Felgner et al., U.S. Pat. Nos. 5,580,859 and 5,703, 055). Administration of DNA vaccines to muscle is also a frequently used method of administration, as is intradermal and subcutaneous injections and transdermal administration. Transdermal administration, such as by iontophoresis, is also an effective method to deliver nucleic acid vaccines to muscle. Epidermal administration of expression vectors of the invention can also be employed. Epidermal administration involves mechanically or chemically irritating the outermost layer of epidermis to stimulate an immune response to the irritant (Carson et al., U.S. Pat. No. 5,679,647).

The vaccines can also be formulated for administration via the nasal passages. Formulations suitable for nasal administration, wherein the carrier is a solid, include a coarse powder having a particle size, for example, in the range of about 10 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active ingredient. For further discussions of nasal administration of AIDS-related vaccines, references are made to the following patents, U.S. Pat. Nos. 5,846,978, 5,663,169, 5,578,597, 5,502,060, 5,476,874, 5,413,999, 5,308,854, 5,192,668, and 5,187,074.

Examples of vaccine compositions of use for the invention include liquid preparations, for orifice, e.g., oral, nasal, anal, vaginal, etc. administration, such as suspensions, syrups or elixirs; and, preparations for parenteral, subcutaneous, intradermal, intramuscular or intravenous administration (e.g., injectable administration) such as sterile suspensions or emulsions. In such compositions the recombinant poxvirus, expression product, immunogen, DNA, or modified gp120 or gp160 may be in admixture with a suitable carrier, diluent, or excipient such as sterile water, physiological saline, glucose or the like.

The vaccines can be incorporated, if desired, into liposomes, microspheres or other polymer matrices (Felgner et al., U.S. Pat. No. 5,703,055; Gregoriadis, *Liposome Technology*, Vols. I to III (2nd ed. 1993), each of which is incorporated herein by reference). Liposomes, for example, which consist of phospholipids or other lipids, are nontoxic, physiologically acceptable and metabolizable carriers that are relatively simple to make and administer.

Liposome carriers may serve to target a particular tissue or infected cells, as well as increase the half-life of the vaccine. Liposomes include emulsions, foams, micelles, insoluble monolayers, liquid crystals, phospholipid dispersions, lamellar layers and the like. In these preparations the vaccine to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes either filled or decorated with a desired immunogen of the invention can be directed to the site of lymphoid cells, where the liposomes then deliver the immunogen(s). Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467 (1980), U.S. Pat. Nos. 4,235,871, 4,501,728, 4,837,028, and 5,019,369.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of noncritical parameters which could be changed or modified to yield essentially similar results.

Example 1

Administration of DNA Priming Vaccines in Combination with NYVAC-SIV$_{gag-pol-env}$ in *Rhesus macaques*

The study design included 24 animals which were divided into three groups, A, B, and C as follows:

Group A: eight animals vaccinated with the nonrecombinant NYVAC control

Group B: eight animals vaccinated with NYVAC-SIV$_{gag-pol-env}$

Group C: eight animals vaccinated with 3 DNA immunizations with 2 constructs expressing the Gag and Env proteins of SIV$_{239}$. followed by inoculation NYVAC-SIV$_{gag-pol-en}$ at the indicated time.

In each group, macaques carrying the MHC class I molecule MAMU-A*01 were included to quantitate the CD3$^+$CD8$^+$ T-cell immune response in the blood. Animals were immunized with either 4 inoculation of 10$^8$ pfu of NYVAC or NYVAC-SIV or with 3 inoculations of DNA (4 mg intramuscularly and 1 mg subcutaneously of each plasmid) followed by two inoculation of NYVAC-SIV at the indicated times (FIG. 1).

The following measure of immune response were obtained:

(1) in vitro lymphoproliferative responses to gp120 and p27 Gag (2) ex vivo percentage of CD3$^+$CD8$^+$ T-cells staining the p11C, C→M-Mamu-A*01 tetramer in peripheral blood monocytes.

(3) expansion of the CD3$^+$CD8$^+$ tetramer-positive population in vitro in the presence of a specific peptide (p11C, C→M)

(4) ELISPOT for γ-IFN secretion following stimulation of CD8$^+$ T-cells with virus-specific nonamers (5) Serum Ab response to the Gag and gp120 env protein antigens can also be measured.

Figure 2:
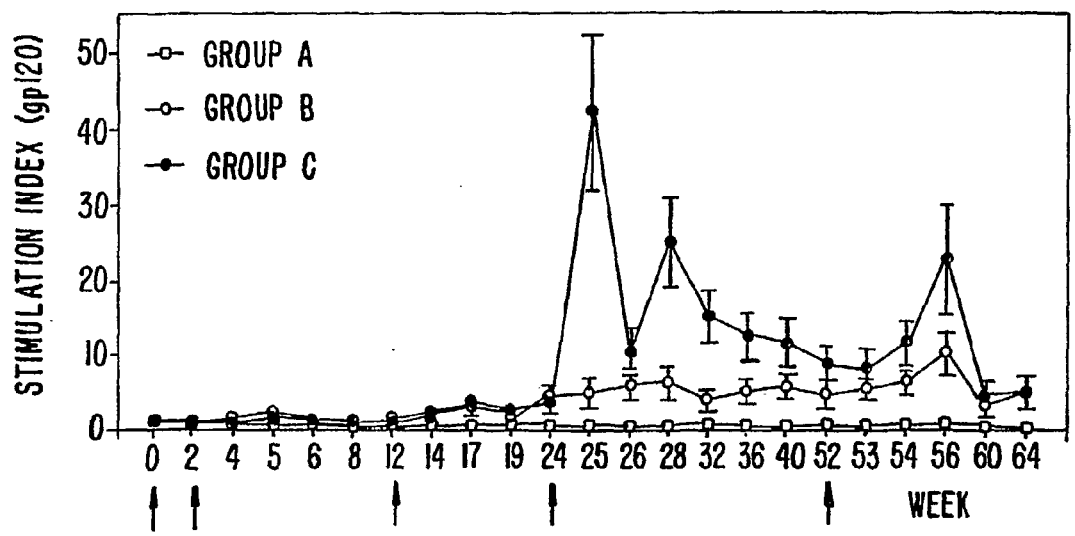
FIG. 2.
Figure 2:
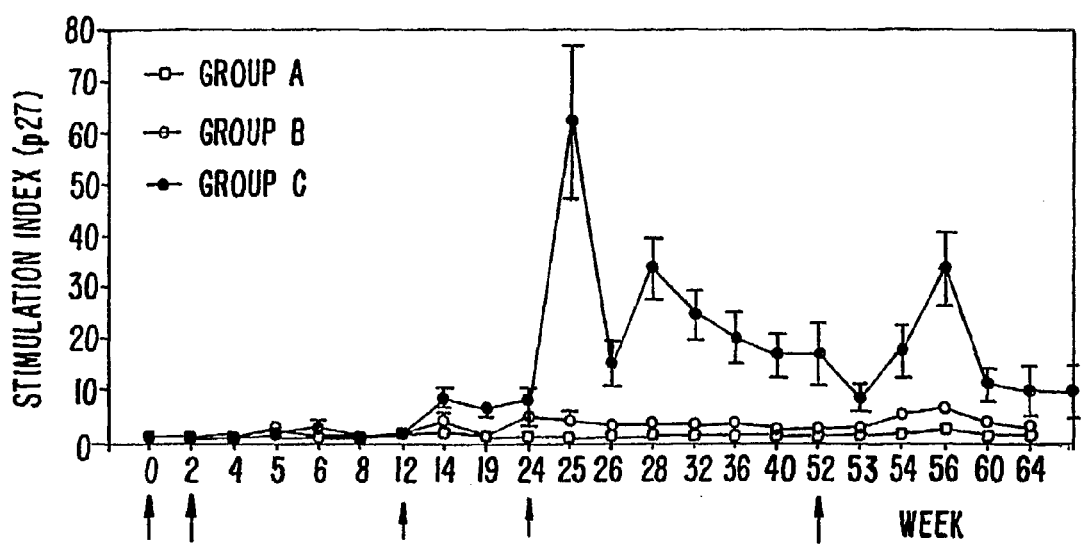

The results showed that low levels of lymphoproliferative responses to p27 Gag and gp120 were observed in animals in group B (FIG. 2) immunized with NYVAC-SIV$_{gag-pol-env}$ alone. A marked lymphoproliferative response was observed in Group C, however. These animals received 3 inoculations of DNA prior to vaccination with NYVAC-SIV$_{gag-pol-env}$. High lymphoproliferative responses to p27 Gag and Env occurred in seven of the eight animals (FIG. 2) and overall, a difference of approximately ten-fold was observed in comparison to group B animals. Additionally, in all of the MAMU-A*01 animals, expansion of the ex vivo and cultured tetramer-positive cells from the blood was observed.

Figure 3:
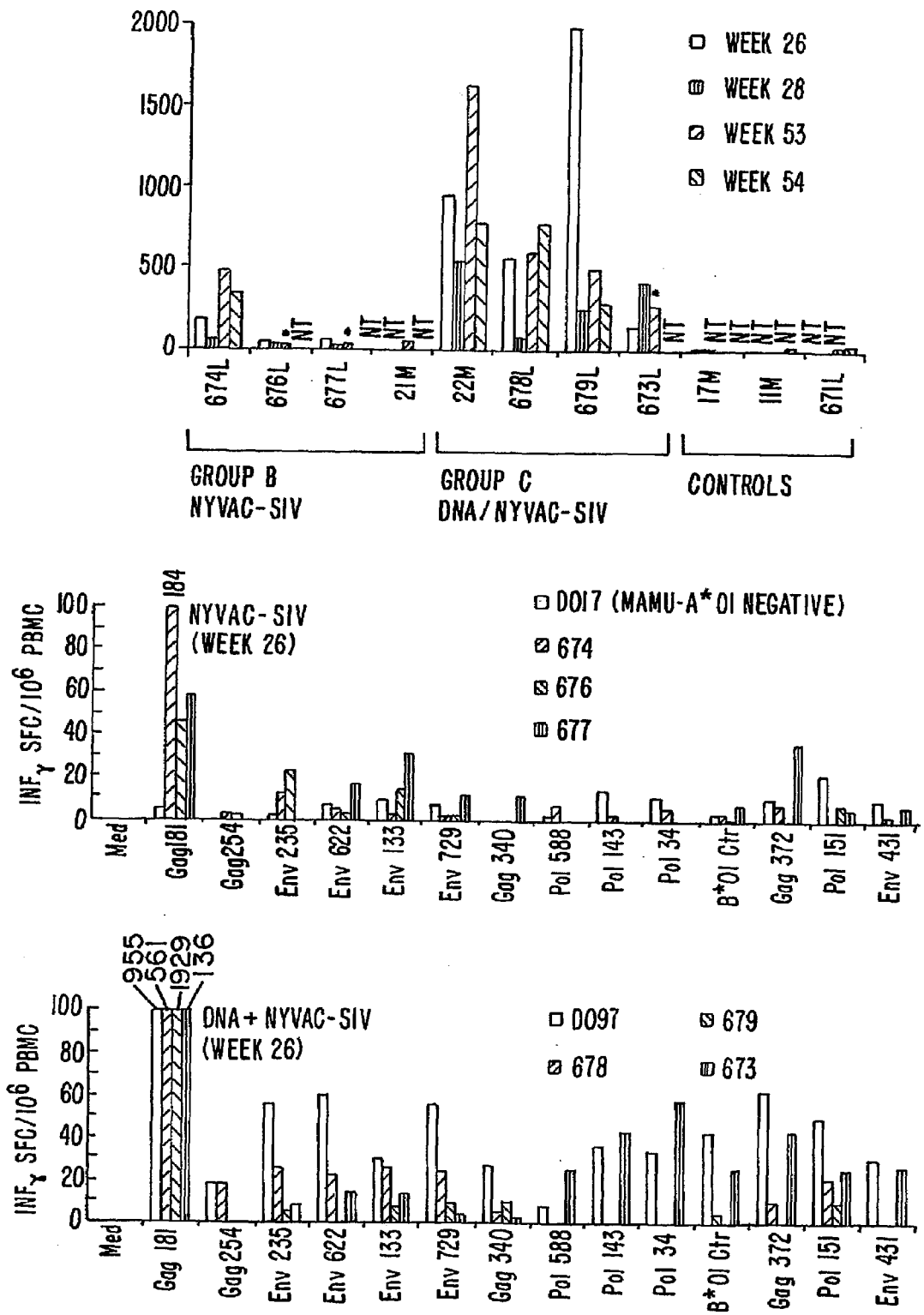
FIG. 3.

To further assess whether DNA priming resulted in potentiation and an increase in breadth of the immune response, ELISPOT analysis of γ-INF-producing cells following a specific peptide stimulation was performed. The results are shown in FIG. 3. The peptides used to stimulate the responses are shown in the X-axes of the middle and bottom panels. An asterisk above the bar (top panel) indicates values obtained by assaying frozen cells (in control experiments, cell freezing decreased the number of peptide-specific spots by 0–20%). Controls include NYVAC-SIV-gpe-vaccinated, MAMU A*01-negative animal 17M, mock NYVAC-vaccinated, MAMU A*01-negative animal 11 M, and mock NYVAC-vaccinated, MAMU A*01-positive animal 671.

The combination of DNA vaccination with NYVAC-SIV vaccination expanded the immunodominant response (p181) in all animals in group C more than 10-fold compared to the animals in group B (FIG. 3, upper panel). These responses were not only of a greater magnitude, but also of longer duration. Moreover, the animals in group C responded to more SIV epitopes and, again, the responses were higher at 2 weeks following immunization (FIG. 3, lower panels).

Figure 4:
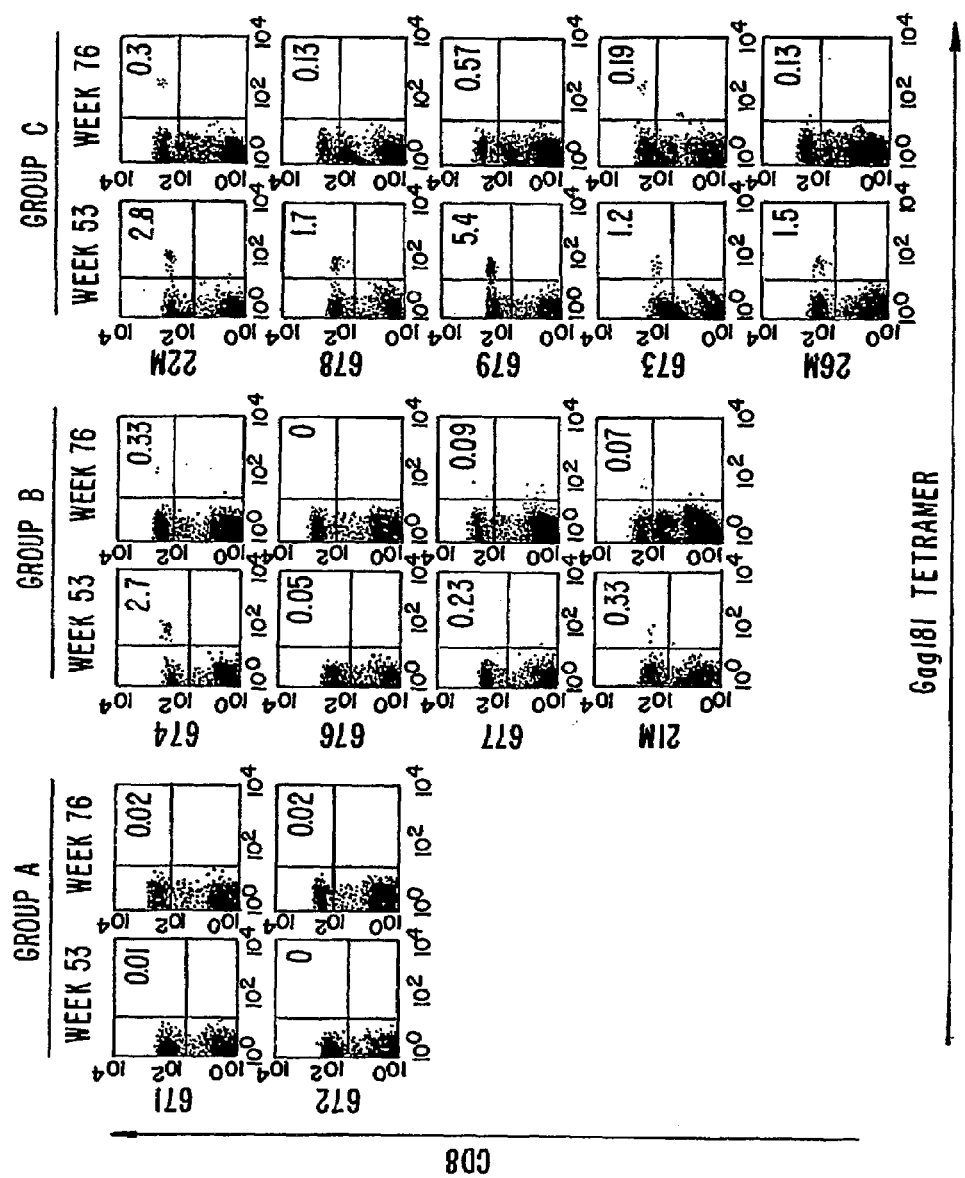
FIG. 4.
Figure 5A:
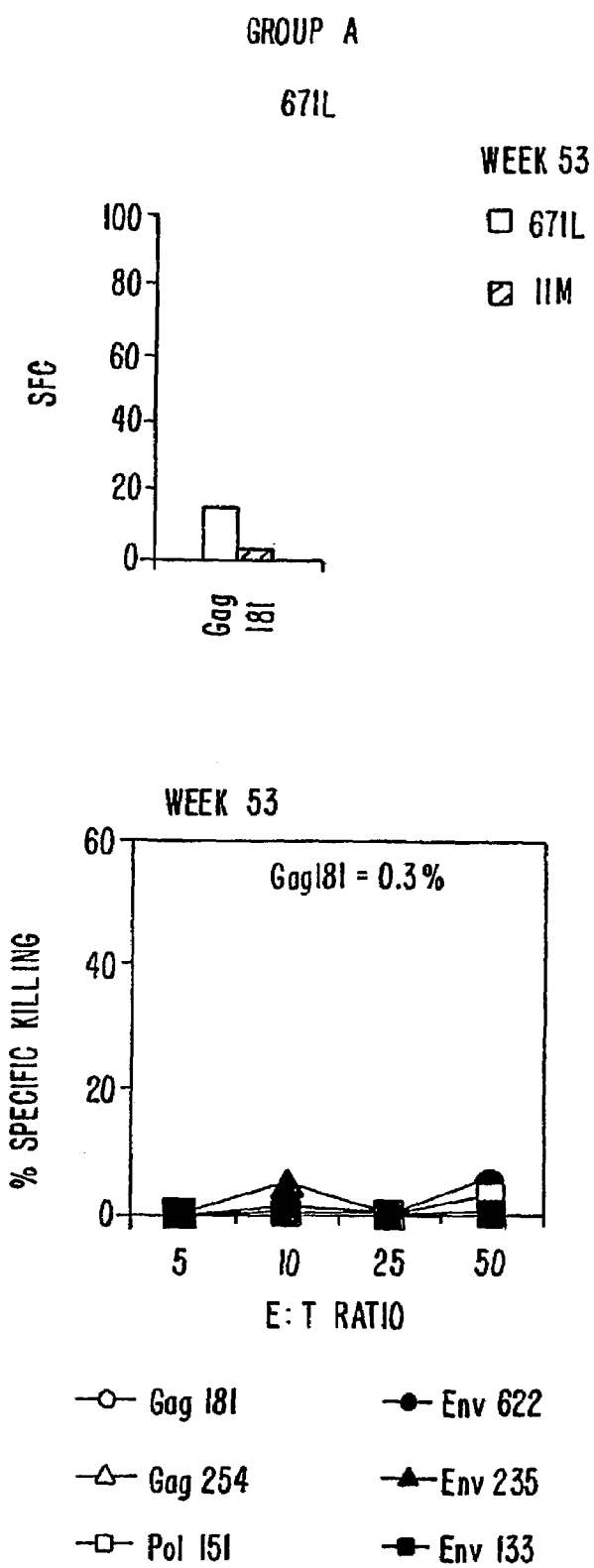
FIG. 5.
Figures 1, 5B:
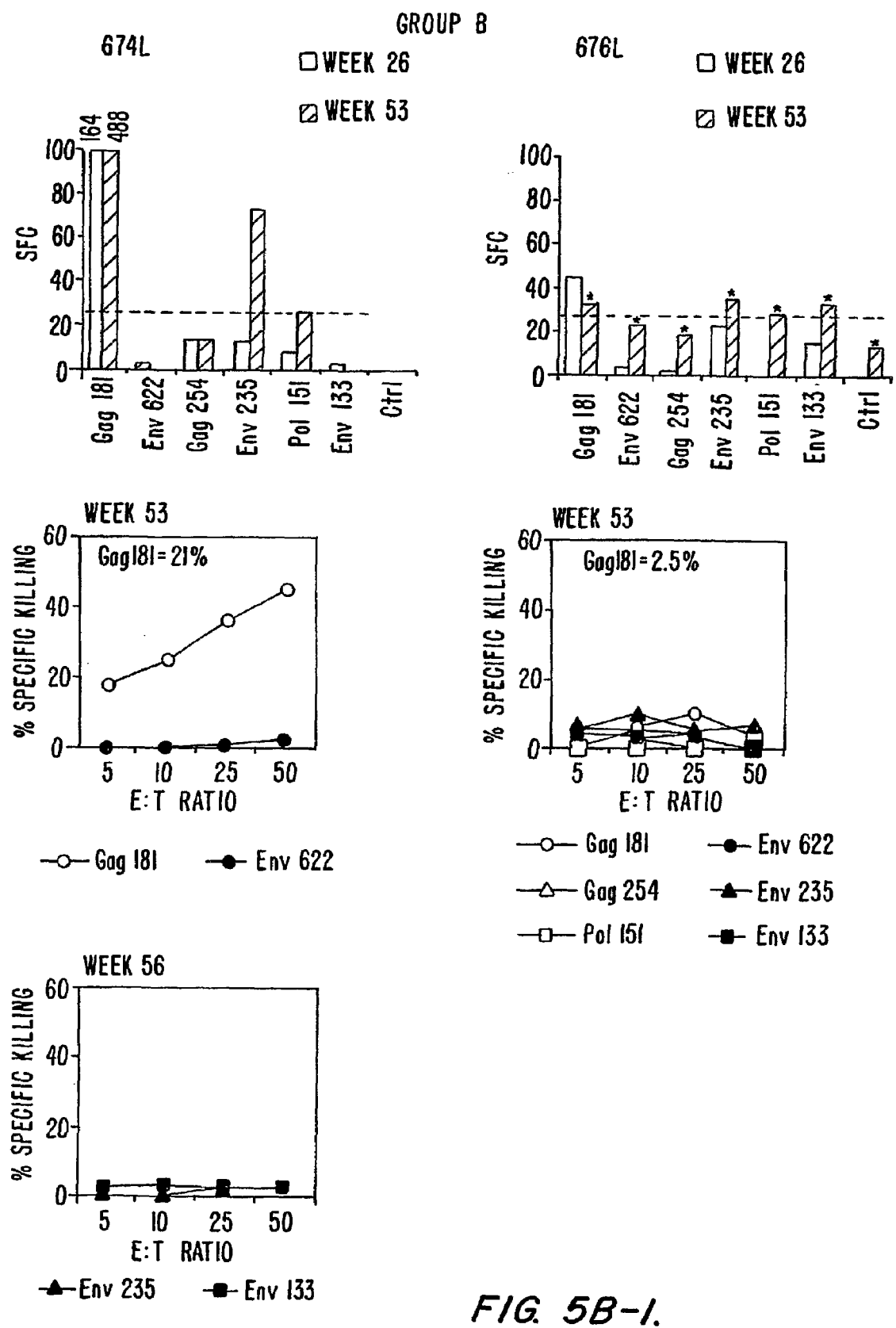
Figures 2, 5B:
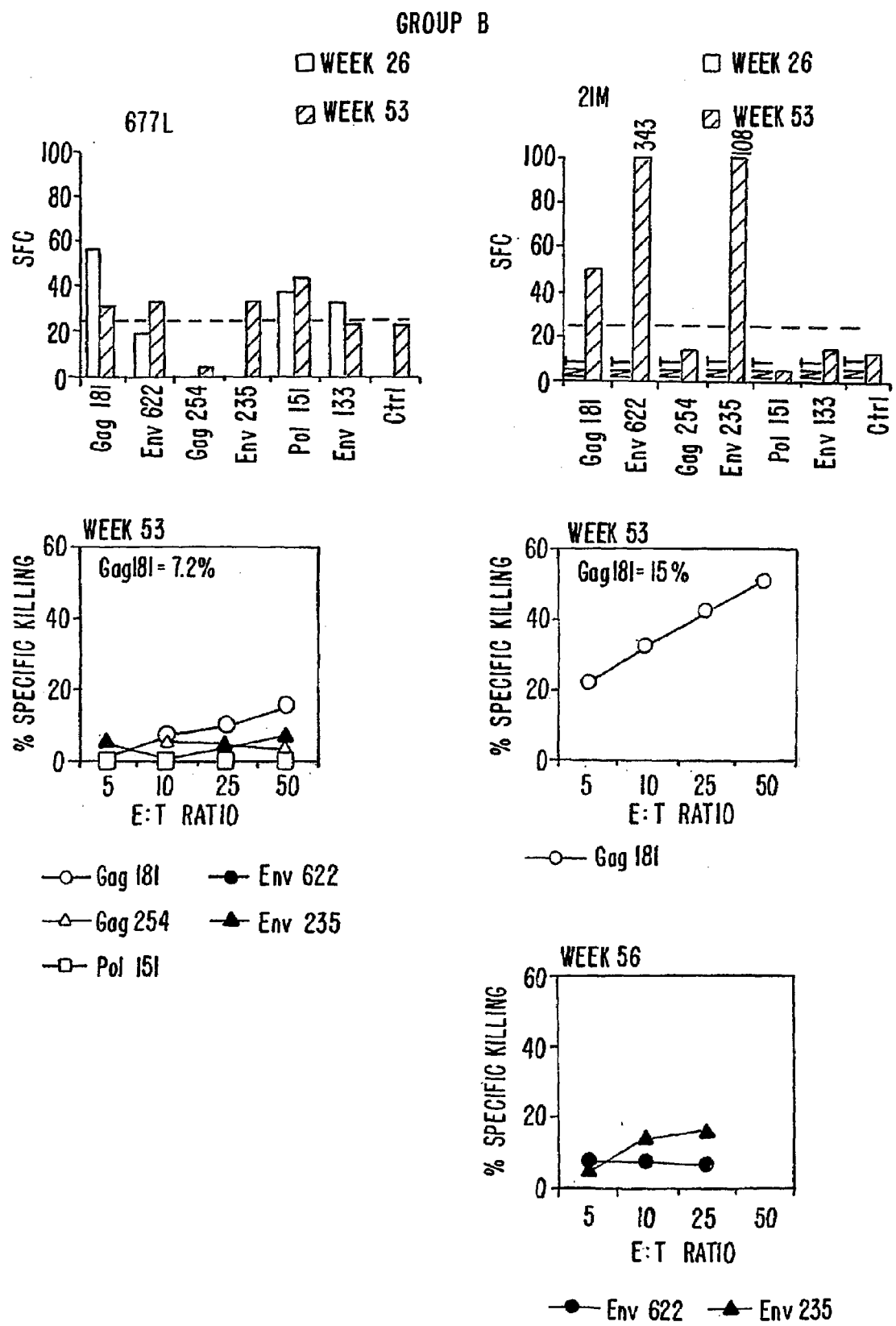
Figure 5C:
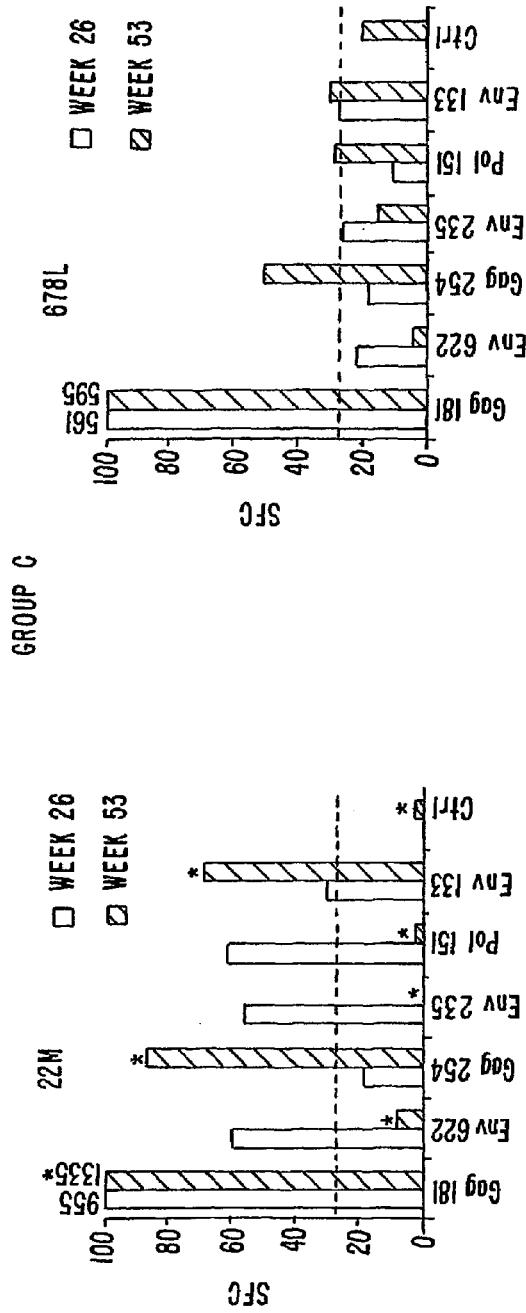
Figure 1:
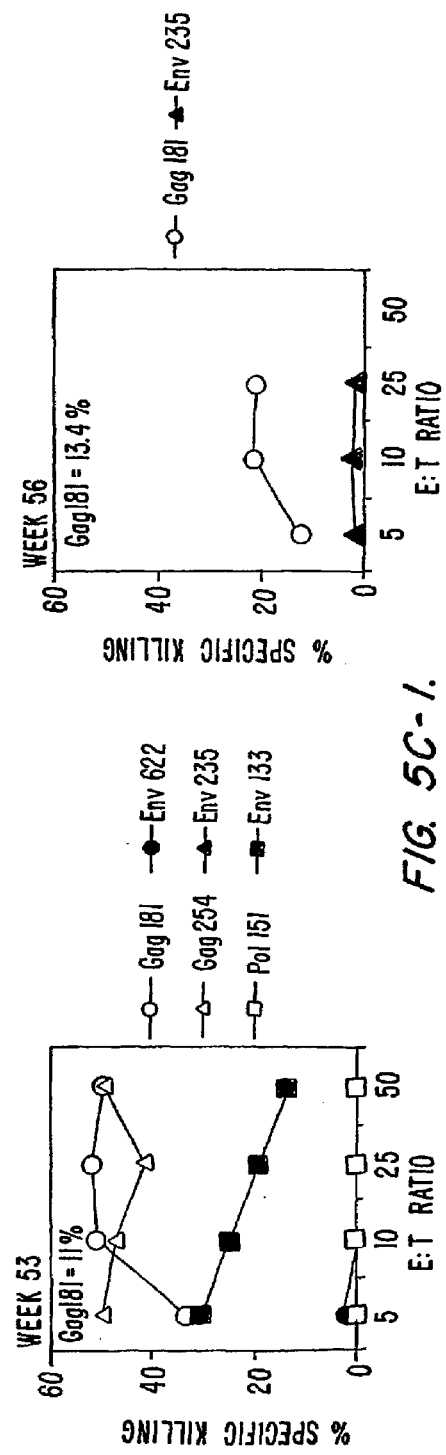
Figures 2, 5C:
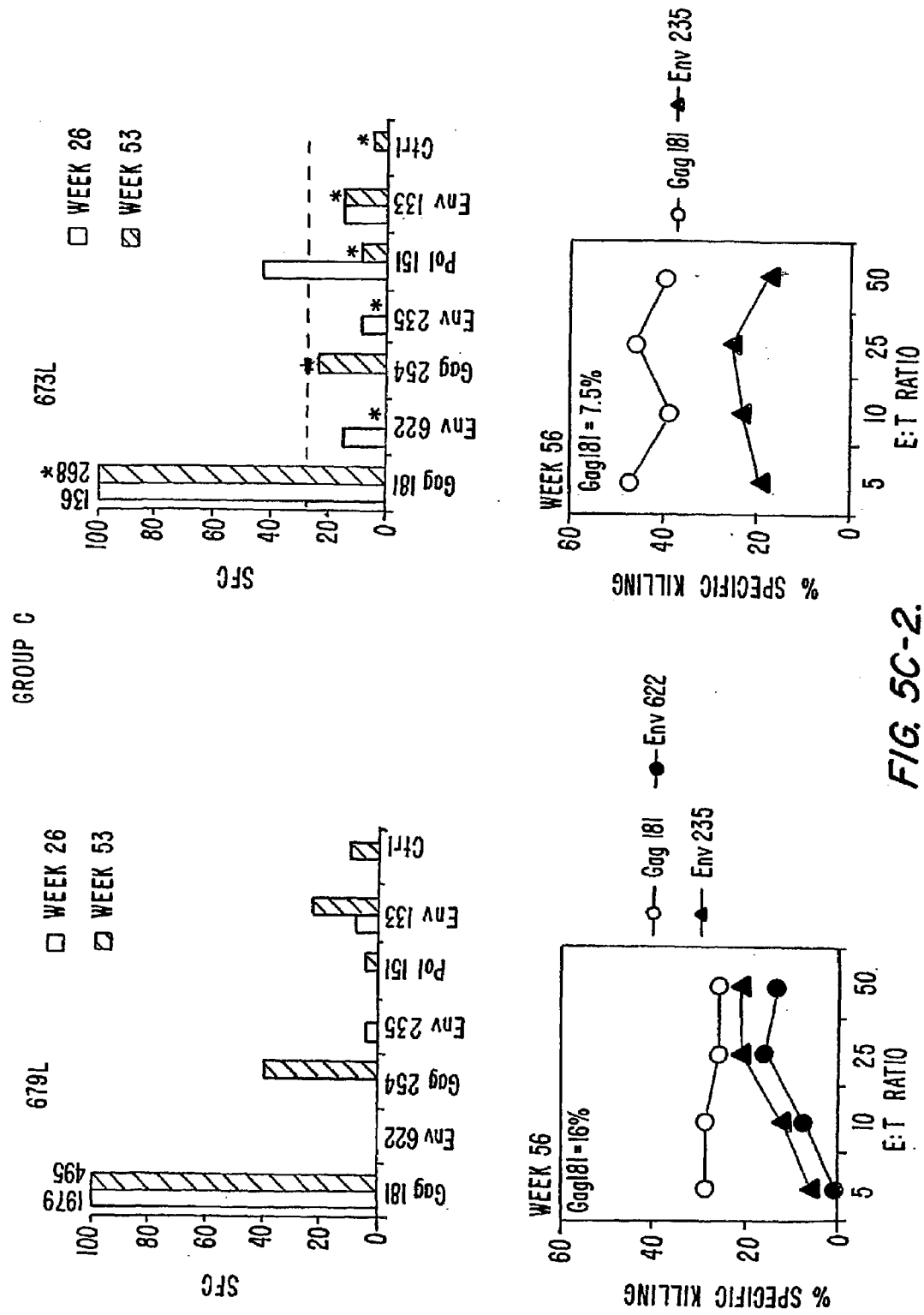
Figure 5C:
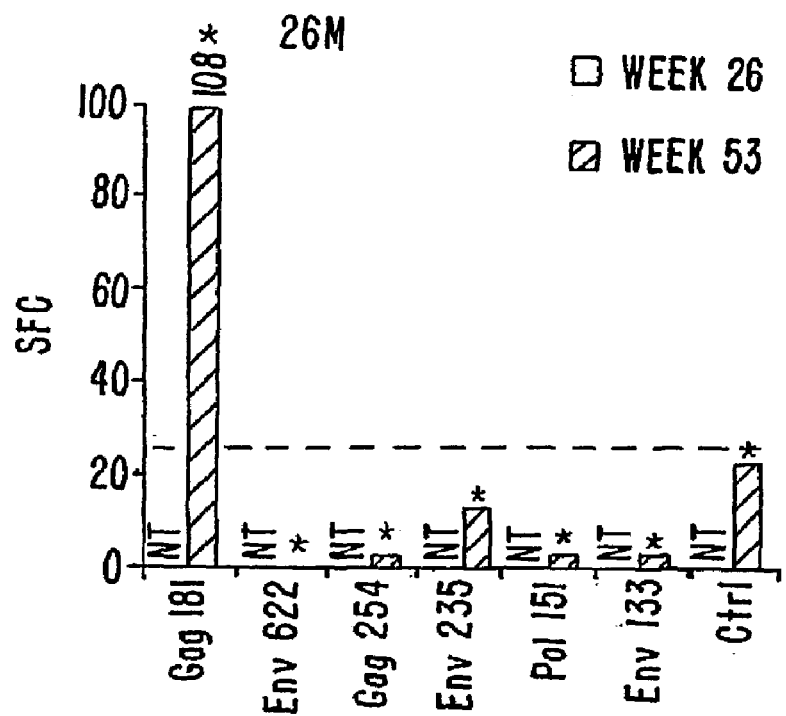
Figure 3:
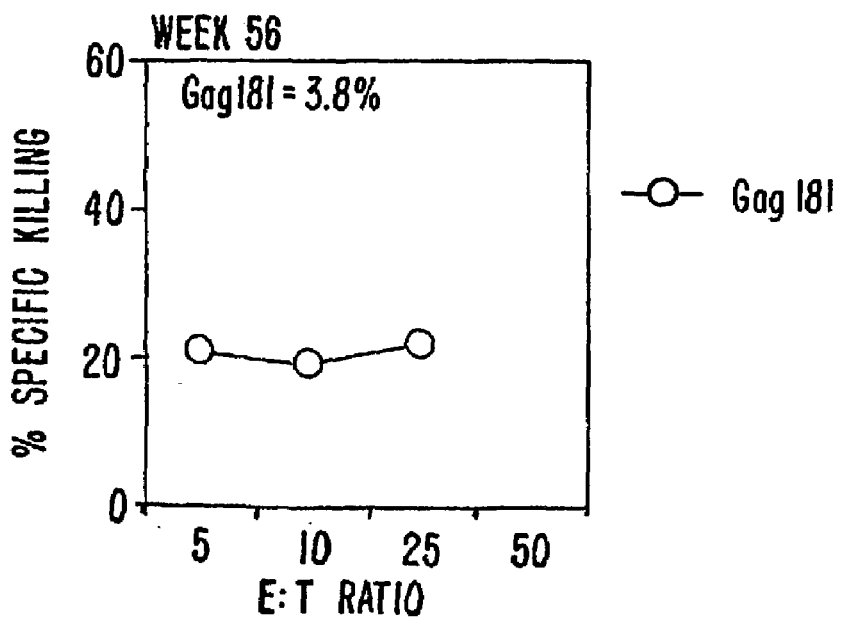

Gag181-specific tetramer staining of fresh PBMC at week 53 and week 76 was also performed. The results (FIG. 4) showed that DNA vaccination also increased the frequency of memory T-cells recognizing the p11C, C→M tetramer, as exemplified by the detection of a clear population of these CD8$^+$ T-cells in the blood of five of five animals of group C and one of four in group B at week 76.

Similarly, the functional activity of these cells in cytolytic assays indicated that five of five macaques in group C had CTL against viral epitopes whereas only two of five in group B did (FIG. 5). The data in FIG. 5 show T-cell responses to various SIV epitopes measured using the ELISPOT and $^{51}$Cr-release assay. The bar charts represent the results of an IFN-γ ELISPOT assays with a specific MAMU A*01-restricted peptide indicated for each set of bars at the indicated times. The values exceeding the chart scale are indicated by number at the top of the bar. Asterisks indicate the values obtained using frozen cells; all other assays were performed using fresh PBMC. "Ctrl" indicates unrelated control peptide; "N.D." indicates not done. Line charts represent the percentage of a specific killing of unpulsed control cells or cells pulsed with a specific MAMU A*01-restricted peptide. All assays were performed using the cells from 7 day cultures with a specific peptide at week 53 or 56, as indicated. "E:T" represents the effector to target cell ratio. The percentage value in the top right corner indicates the percentage of Gag181 tetramer-staining CD3$^+$CD8$^+$ cells in culture PBMC.

Figure 6:
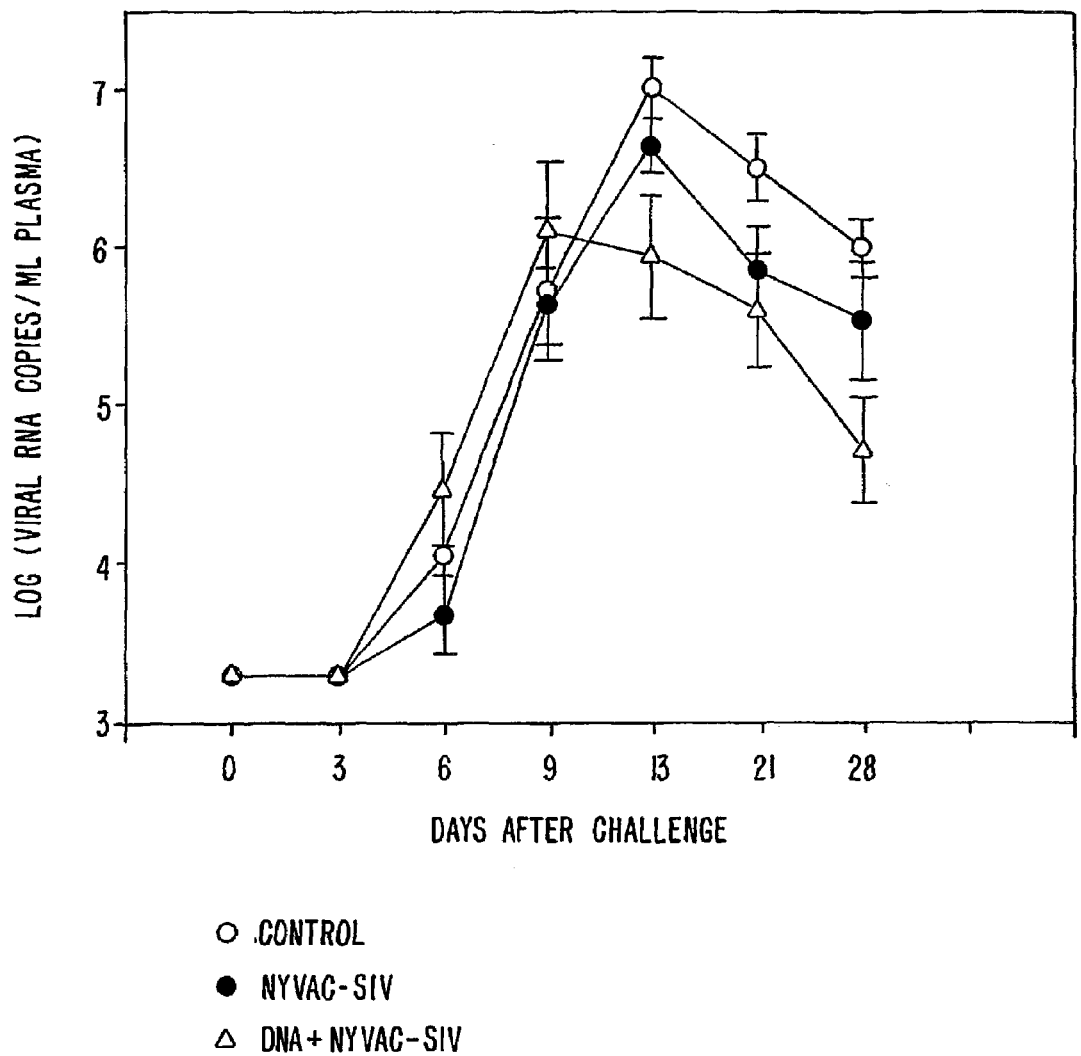
FIG. 6.
Figure 7:
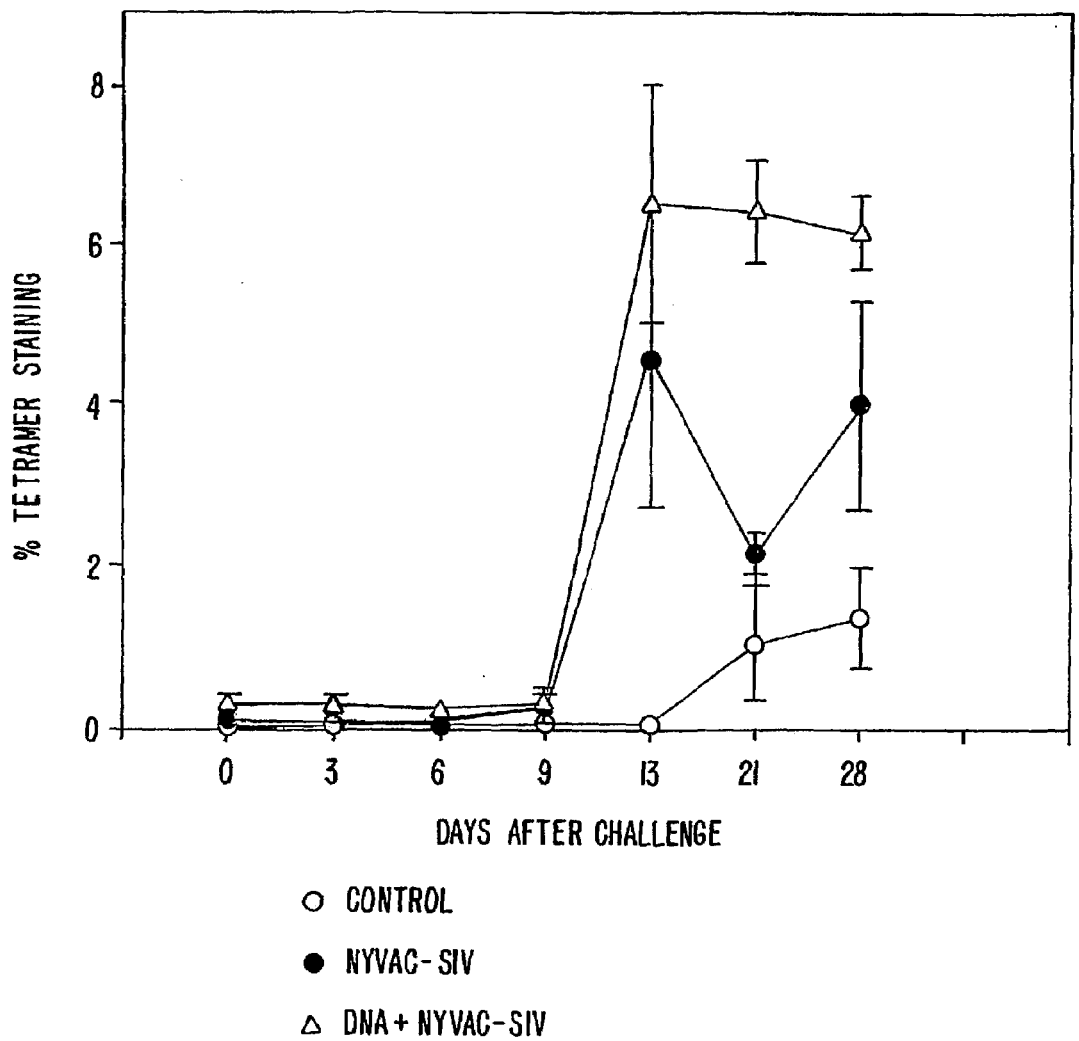
FIG. 7.

Following intrarectal challenge with the highly pathogenic SIV$_{mac251\ (561)}$ strain, most animals became viremic except one of the animals in group C. The ability of vaccinated animals to suppress viremia was assessed within the first 28 days and, as demonstrated in FIG. 6, macaques immunized with DNA at first were better able to control viremia than control macaques. Interestingly, quantification of the anamnestic response in vaccinated animals using the Gag 181 tetramer indicated that in DNA primed animals, the response was higher and sustained (FIG. 7).

Figure 8:
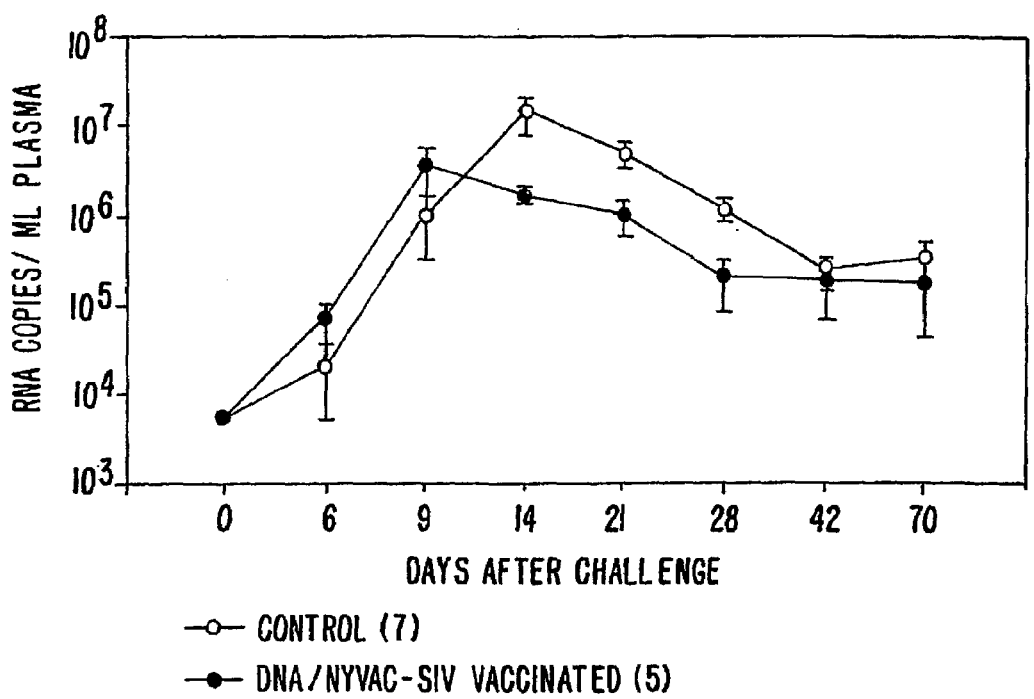
FIG. 8.
Figure 8:
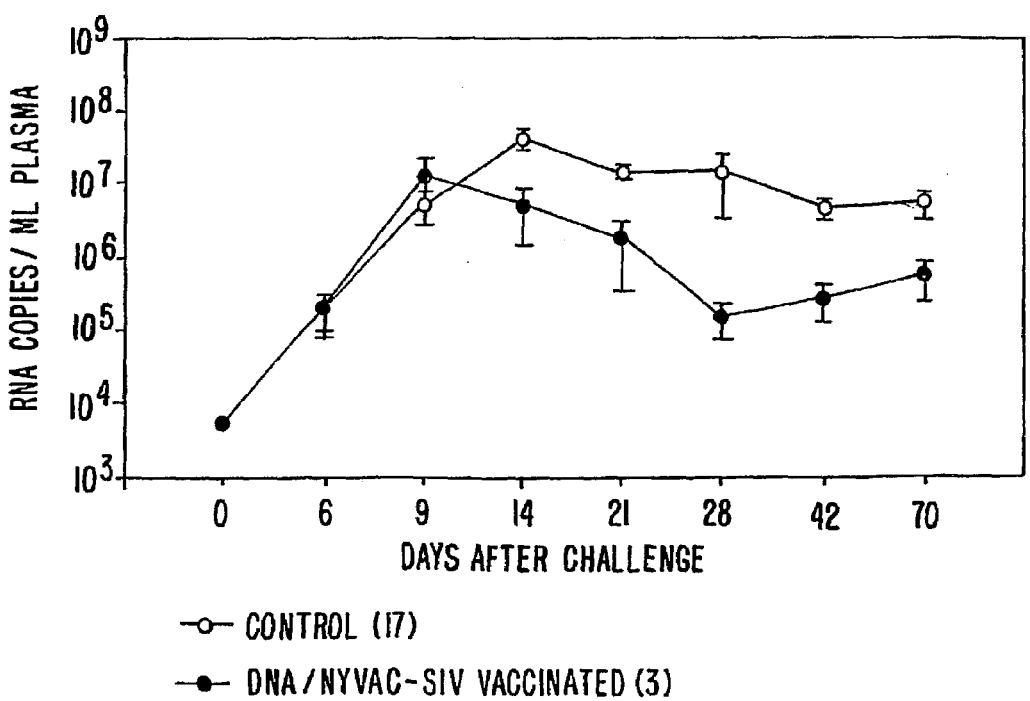

Because it has been previously demonstrated that Mamu-A*01-positive animals are genetically advantaged and better control viremia than Mamu-A*01-negative animals, virus load and anamnestic response were investigated independently in Mamu-A*01-positive and -negative macaques. As demonstrated in FIG. 8, analysis of virus load in Mamu-A*01-positive control animals (including data from historical control animals challenged with the same virus stock by the same route to increase the statistical power of our analyses) and vaccinated animals in group C demonstrated a vaccine effect, and a similar effect was observed in Mamu-A*01-negative macaques (bottom panel). Thus, DNA vaccination ameliorated the virological outcome even in animals without an inherent genetic predisposition to control viremia.

Data in the literature indicated that DNA priming followed by MVA boost was not so effective in reducing virus load (see, e.g., Hanke et al., *J. Virol.* 73:7524–7532, 1999). The demonstration that DNA in combination with NYVAC significantly improved viral outcome was surprising and may be dependent on inherent features of this poxvirus vector.

These data demonstrate that DNA vaccination greatly potentiates and increases the breadth of the immune response induced by a NYVAC-based vaccine and shows that this vaccine combination increases the immunogenicity and efficacy of the highly attenuated poxvirus vectors.

ALVAC-based vaccine are similarly analyzed demonstrating that they also potentiate the immune response when used in conjunction with DNA vaccines.

Example 2

Administration to a Person

A vaccine regimen of a DNA priming vaccine followed by innoculation with a vaccine such as NYVAC or ALVAC, is used prophylactically in individuals at risk for HIV infection. (Such a vaccine regimen can also be used therapeutically for HIV-infected patients).

The individual is injected with a DNA priming vaccine that, e.g, expresses the HIV-1 gag, pro, tat, nef, rev, and env genes. Multiple priming inoculations are typically administered. The amount of DNA administered is typically 800 μg intramuscularly or 200 μg intradermally. After an interval determined by the physician, the patient is subsequently injected with a vaccine comprising about $10^8$ pfu of a recombinant pox virus, e.g. NYVAC, expressing HIV-1 gag, pro, tat, nef, rev, and env epitopes.

The patient's immune response is evaluated ($CD4^+$ proliferative response, cytotoxic $CD8^+$ T-cell activity, etc.) and a decision is made as to whether and when to immunize again.

The combination of administration of the DNA vaccine followed by immunization with the recombinant NYVAC vaccine provides a protective immune response in uninfected patients and a therapeutic effect in those individuals already infected with HIV-1.

What is claimed is:

1. A method of potentiating a CD8+ response to human immunodeficiency virus-1 (HIV-1) epitopes in a human comprising:
    administering an expression vector encoding HIV-1 Gag, Pol, Pro, Tat, Nef, Rev, Vif, Vpr or Env antigens; and
    administering a recombinant NYVAC pox virus encoding the same antigens encoded by the expression vector;
    wherein the expression vector and the recombinant pox virus enter the cells of the human and intracellularly produce HIV peptides that are presented on the cell's MHC class I molecules in an amount sufficient to stimulate a CD8+ response, and further, wherein administration of the combination of the expression vector and the recombinant pox virus potentiates the immune response compared to administration of either the expression vector or the recombinant pox virus by itself.

2. A method of claim 1 wherein the recombinant pox virus is an attenuated recombinant pox virus vaccine.

3. A method of claim 1, wherein the expression vector is a DNA expression vector.

4. A method of claim 1 wherein the HIV peptides are structural viral peptides.

5. A method of claim 1 wherein the HIV peptides are non-structural viral peptides.

6. A method of claim 1 wherein the expression vector or the recombinant NYVAC pox virus is administered with an adjuvant.

7. A method of claim 1 further comprising two administrations of the expression vector.

8. A method of claim 7 comprising three administrations of the expression vector.

9. A method of claim 1, wherein the expression vector is administered before the recombinant pox virus.

10. A method of claim 1, wherein the human is infected with HIV-1.

11. A method of claim 10, wherein the human has a viral load of less than 10,000 copies per milliliter.

12. A method of claim 1, wherein the human is not infected with the HIV-1.

13. The method of claim 1, wherein the HIV peptides are HIV-1 envelope, gag or protease peptides.

14. A method of reducing viral load in a mammal that may be infected with an immunodeficiency virus, comprising:
    administering to the mammal an expression vector that expresses encoded immunodeficiency virus Gag, Pol and Env antigens; and
    later administering to the mammal a recombinant NYVAC pox virus encoding said antigens;
    wherein the expression vector and the recombinant pox virus enter the cells of the mammal and intracellularly produce said antigens, and
    wherein admininstration of the combination of the expression vector and the recombinant pox virus reduces the viral load more than administration of either the expression vector or the recombinant pox virus by itself.

* * * * *

UNITED STATES PATENT AND TRADEMARK OFFICE
CERTIFICATE OF CORRECTION

PATENT NO. : 7,094,408 B2
APPLICATION NO. : 10/258570
DATED : August 22, 2006
INVENTOR(S) : Franchini et al.

It is certified that error appears in the above-identified patent and that said Letters Patent is hereby corrected as shown below:

On the Title page, in Item (75), in "Inventors", in column 1, line 4, after "(US)" insert -- ; James Tartaglia, Aurora, Ontario Canada (US) --.

On the Title page, in Item (73), in "Assignee", in column 1, lines 1-4, delete "The United States of America as represenetd by the Department of Health and Human Services, Washington, DC (US)" and insert -- Government of the United States of America as represented by the Secretary of the Department of Health and Human Services, Rockville, Maryland (US) --, therefor.

On the Title page, in Item (56), under "Other Publications, in column 2, line 13, delete "APronounced" and insert -- A Pronounced --, therefor.

On the Title page, in Item (57), under "Abstract", in column 2, line 8, delete "virus," and insert -- , --, therefor.

On page 2, in Item (56), under "Other Publications", in column 1, line 38, delete "Therary" and insert -- Therapy --, therefor.

On page 2, in Item (56), under "Other Publications", in column 1, line 41, delete "Progagation" and insert -- Propagation --, therefor.

On page 2, in Item (56), under "Other Publications", in column 1, line 70, delete "Lymphoctyes" and insert -- Lymphocytes --, therefor.

On page 2, in Item (56), under "Other Publications", in column 2, line 10, delete "Enchanced" and insert -- Enhanced --, therefor.

On page 2, in (56), under "Other Publications", in column 2, line 39, delete "SIV $_{mac}$ -Induced" and insert -- SIV$_{mac}$-Induced --, therefor.

On page 3, in (56), under "Other Publications", in column 1, line 25, delete "Exp" and insert -- Exp. --, therefor.

On page 3, in (56), under "Other Publications", in column 1, line 35, delete "envirev" and insert -- envlrev --, therefor.

Column 1, line 8, after "application" insert -- is a national stage application of PCT/US01/13968 which --.

UNITED STATES PATENT AND TRADEMARK OFFICE
CERTIFICATE OF CORRECTION

PATENT NO. : 7,094,408 B2
APPLICATION NO. : 10/258570
DATED : August 22, 2006
INVENTOR(S) : Franchini et al.

It is certified that error appears in the above-identified patent and that said Letters Patent is hereby corrected as shown below:

Column 2, lines 31-32, delete "SIV-mac251." and insert -- $SIV_{mac251}$ .--, therefor.

Column 4, line 6, delete "SIV gpe" and insert -- SIVgpe --, therefor.

Column 4, line 17, delete "Sci" and insert -- Sci. --, therefor.

Column 4, line 20, delete "fowl pox" and insert -- fowlpox --, therefor.

Column 4, line 22, delete "et al," and insert -- et al., --, therefor.

Column 5, line 12, delete "vaccinee" and insert -- vaccine --, therefor.

Column 7, line 11, delete "vif and" and insert --vif, and --, therefor.

Column 7, line 32, delete "et. al." and insert -- et al. --, therefor.

Column 8, line 29, after "Epitope" delete ".".

Column 8, line 36, after "constructs can" delete "can".

Column 8, line 65, delete "CD4+" and insert -- $CD4^+$ --, therefor.

Column 9, line 12, after "to as" delete ""immunophenotyping" and insert -- immunophenotyping --, therefor.

Column 9, line 66, delete "lymphoidne" and insert -- lymphokine --, therefor.

Column 10, line 9, delete "Vol" and insert -- Vol. --, therefor.

Column 10, line 20, delete "[NASBA®]," and insert -- [NASBA®], --, therefor.

Column 10, line 27, delete "NASBA®" and insert -- NASBA® --, therefor.

Column 13, line 34, after "$SIV_{239}$." delete "followed" and insert -- Followed --, therefor.

Column 14, lines 39-40, delete "$^5$1 Cr" and insert -- $^{51}$Cr --, therefor.

Column 14, line 64, delete "Gag 181" and insert -- Gag181 --, therefor.

Column 15, line 42, delete "e.g," and insert -- e.g., --, therefor.

UNITED STATES PATENT AND TRADEMARK OFFICE
CERTIFICATE OF CORRECTION

PATENT NO. : 7,094,408 B2
APPLICATION NO. : 10/258570
DATED : August 22, 2006
INVENTOR(S) : Franchini et al.

It is certified that error appears in the above-identified patent and that said Letters Patent is hereby corrected as shown below:

Column 16, line 2, in Claim 1, delete "CD8+" and insert -- $CD8^+$ --, therefor.

Column 16, line 12, in Claim 1, delete "CD8+" and insert -- $CD8^+$ --, therefor.

Column 16, line 53, in Claim 14, delete "administration" and insert -- administration --, therefor.

Signed and Sealed this

Tenth Day of April, 2007

JON W. DUDAS
*Director of the United States Patent and Trademark Office*

UNITED STATES PATENT AND TRADEMARK OFFICE
CERTIFICATE OF CORRECTION

PATENT NO. : 7,094,408 B2  Page 1 of 1
APPLICATION NO. : 10/258570
DATED : August 22, 2006
INVENTOR(S) : Genoveffa Franchini et al.

It is certified that error appears in the above-identified patent and that said Letters Patent is hereby corrected as shown below:

On the Title page, in Item (73) Assignee, column 1, line 4, after (US), insert,
--Aventis Pasteur, Inc., Toronto, Ontario, Canada--

Signed and Sealed this

Twenty-second Day of June, 2010

David J. Kappos
*Director of the United States Patent and Trademark Office*